(12) United States Patent
Jónsson

(10) Patent No.: US 8,486,156 B2
(45) Date of Patent: Jul. 16, 2013

(54) PROSTHETIC FOOT WITH A CURVED SPLIT

(75) Inventor: Vilhjalmur Freyr Jónsson, Reykjavik (IS)

(73) Assignee: Össur hf, Reykjavik (IS)

( * ) Notice: Subject to any disclaimer, the term of this patent is extended or adjusted under 35 U.S.C. 154(b) by 111 days.

(21) Appl. No.: 13/034,474

(22) Filed: Feb. 24, 2011

(65) Prior Publication Data

US 2011/0213471 A1 Sep. 1, 2011

Related U.S. Application Data

(60) Provisional application No. 61/308,818, filed on Feb. 26, 2010.

(51) Int. Cl.
*A61F 2/68* (2006.01)

(52) U.S. Cl.
USPC ............................................ 623/53; 623/55

(58) Field of Classification Search
USPC ........................................................ 623/53
See application file for complete search history.

(56) References Cited

U.S. PATENT DOCUMENTS

| | | |
|---|---|---|
| 25,238 A | 8/1859 | Bly |
| 53,931 A | 4/1866 | Weston et al. |
| 56,931 A | 8/1866 | Nicholas |
| 57,666 A | 9/1866 | Bly |
| 368,580 A | 8/1887 | Frees |
| 487,697 A | 12/1892 | Ehle |
| 534,198 A | 2/1895 | Chapman |
| 619,731 A | 2/1899 | Doerflinger et al. |
| 808,296 A | 12/1905 | Merrick |
| 809,876 A | 1/1906 | Wilkins |
| 817,340 A | 4/1906 | Rosenkranz |
| 2,183,076 A | 12/1939 | Kaiser |
| 2,197,093 A | 4/1940 | Campbell |
| 2,315,795 A | 4/1943 | Johnson et al. |

(Continued)

FOREIGN PATENT DOCUMENTS

| | | |
|---|---|---|
| WO | WO 98/53769 | 12/1998 |
| WO | WO 00/27317 | 5/2000 |

(Continued)

OTHER PUBLICATIONS

2009/0287315 and its ongoing prosecution history, including without limitation Office Actions, Amendments, Remarks, and any other potentially relevant documents.
Apr. 25, 2011 International Search Report and Written Opinion for International Application No. PCT/US11/26124 filed Feb. 24, 2011.
Endolite EliteVT product; Catalog Page available at http://www.endolite.com/products/feet/eliteVT.php, believed to have been launched approximately Feb. 2009.

(Continued)

*Primary Examiner* — David Isabella
*Assistant Examiner* — Jacqueline Woznicki
(74) *Attorney, Agent, or Firm* — Knobbe, Martens, Olson & Bear, LLP

(57) ABSTRACT

Prosthetic feet having a split feature are described. The prosthetic feet can include a plate-like upper element and a plate-like lower element connected to the upper element. The plate-like upper element can include a split that separates the upper element into a medial blade and a lateral blade. A portion of the split can curve in a medial or lateral direction. Portions of the split can also be straight, but askew, from a longitudinal axis of the upper element. The plate-like lower element can also include a similar curved split that separates the lower element into a medial blade and a lateral blade. These features, among others, are designed to provide multi-axial movement capabilities of a natural human foot and enhance roll-over properties while in use.

14 Claims, 36 Drawing Sheets

U.S. PATENT DOCUMENTS

| | | |
|---|---|---|
| 2,357,893 A | 9/1944 | Harrington |
| 2,594,945 A | 4/1952 | Lucas et al. |
| 2,692,392 A | 10/1954 | Bennington et al. |
| 2,731,645 A | 1/1956 | Woodall |
| 3,551,914 A | 1/1971 | Woodall |
| 3,784,988 A | 1/1974 | Trumpler |
| 3,874,004 A | 4/1975 | May |
| 4,007,497 A | 2/1977 | Haupt |
| 4,360,931 A | 11/1982 | Hampton |
| 4,387,472 A | 6/1983 | Wilson |
| 4,547,913 A | 10/1985 | Phillips |
| 4,718,913 A | 1/1988 | Voisin |
| 4,822,363 A | 4/1989 | Phillips |
| 4,892,553 A | 1/1990 | Prahl |
| 4,892,554 A | 1/1990 | Robinson |
| 4,959,073 A | 9/1990 | Merlette |
| 5,019,109 A | 5/1991 | Voisin |
| 5,037,444 A | 8/1991 | Phillips |
| 5,062,859 A | 11/1991 | Naeder |
| 5,112,356 A | 5/1992 | Harris et al. |
| 5,116,384 A | 5/1992 | Wilson et al. |
| 5,139,525 A | 8/1992 | Kristinsson |
| 5,156,631 A | 10/1992 | Merlette |
| 5,181,932 A | 1/1993 | Phillips |
| 5,181,933 A | 1/1993 | Phillips |
| 5,219,365 A | 6/1993 | Sabolich |
| 5,258,038 A | 11/1993 | Robinson et al. |
| 5,258,039 A | 11/1993 | Goh et al. |
| 5,290,319 A | 3/1994 | Phillips |
| 5,376,133 A | 12/1994 | Gramnas |
| 5,376,141 A | 12/1994 | Phillips |
| 5,387,246 A | 2/1995 | Phillips |
| 5,425,781 A | 6/1995 | Allard et al. |
| 5,443,522 A | 8/1995 | Hiemisch |
| 5,443,527 A | 8/1995 | Wilson |
| 5,443,529 A | 8/1995 | Phillips |
| 5,509,938 A | 4/1996 | Phillips |
| 5,514,185 A | 5/1996 | Phillips |
| 5,545,234 A | 8/1996 | Collier, Jr. |
| 5,653,767 A | 8/1997 | Allen et al. |
| 5,695,526 A | 12/1997 | Wilson |
| 5,695,527 A | 12/1997 | Allen |
| 5,701,686 A | 12/1997 | Berr et al. |
| 5,728,177 A | 3/1998 | Phillips |
| 5,766,264 A | 6/1998 | Lundt |
| 5,800,569 A | 9/1998 | Phillips |
| 5,824,112 A | 10/1998 | Phillips |
| 5,897,594 A | 4/1999 | Martin et al. |
| 5,899,944 A | 5/1999 | Phillips |
| 5,941,913 A | 8/1999 | Woolnough et al. |
| 5,944,760 A | 8/1999 | Christensen |
| 5,957,981 A | 9/1999 | Gramnas |
| 5,993,488 A | 11/1999 | Phillips |
| 6,071,313 A | 6/2000 | Phillips |
| 6,099,572 A | 8/2000 | Mosler et al. |
| 6,120,547 A | 9/2000 | Christensen |
| 6,129,766 A | 10/2000 | Johnson et al. |
| 6,165,227 A | 12/2000 | Phillips |
| 6,197,068 B1 | 3/2001 | Christensen |
| 6,206,934 B1 | 3/2001 | Phillips |
| 6,241,776 B1 | 6/2001 | Christensen |
| 6,261,324 B1 | 7/2001 | Merlette |
| 6,280,479 B1 | 8/2001 | Phillips |
| 6,290,730 B1 | 9/2001 | Pitkin et al. |
| 6,350,286 B1 | 2/2002 | Atkinson et al. |
| 6,387,134 B1 | 5/2002 | Parker et al. |
| 6,398,818 B1 | 6/2002 | Merlette et al. |
| 6,402,790 B1 | 6/2002 | Celebi |
| 6,443,993 B1 | 9/2002 | Koniuk |
| 6,443,995 B1 | 9/2002 | Townsend et al. |
| 6,596,029 B1 | 7/2003 | Gramnas |
| 6,663,672 B1 | 12/2003 | Laghi |
| 6,663,673 B2 | 12/2003 | Christensen |
| 6,676,708 B1 | 1/2004 | Laghi |
| 6,699,295 B2 | 3/2004 | Lee et al. |
| 6,702,859 B1 | 3/2004 | Laghi |
| 6,702,860 B1 | 3/2004 | Laghi |
| 6,706,075 B1 | 3/2004 | Laghi |
| 6,712,860 B2 | 3/2004 | Rubie et al. |
| 6,718,656 B2 | 4/2004 | Houser et al. |
| 6,719,807 B2 | 4/2004 | Harris |
| 6,764,521 B2 | 7/2004 | Molino et al. |
| 6,764,522 B1 | 7/2004 | Cehn |
| 6,767,370 B1 | 7/2004 | Mosler et al. |
| 6,793,683 B1 | 9/2004 | Laghi |
| 6,797,009 B1 | 9/2004 | Laghi |
| 6,805,717 B2 | 10/2004 | Christensen |
| 6,827,744 B1 | 12/2004 | Laghi |
| 6,855,170 B2 | 2/2005 | Gramnas |
| 6,869,451 B1 | 3/2005 | Laghi |
| 6,875,240 B1 | 4/2005 | Laghi |
| 6,875,241 B2 | 4/2005 | Christesen |
| 6,875,242 B2 | 4/2005 | Christensen |
| 6,899,737 B1 | 5/2005 | Phillips |
| 6,929,665 B2 | 8/2005 | Christensen |
| 6,966,933 B2 | 11/2005 | Christensen |
| 6,969,408 B2 | 11/2005 | Lecomte et al. |
| 7,052,519 B1 | 5/2006 | Gramnas |
| 7,063,727 B2 | 6/2006 | Phillips et al. |
| 7,108,723 B2 | 9/2006 | Townsend et al. |
| 7,169,190 B2 | 1/2007 | Phillips et al. |
| 7,211,115 B2 | 5/2007 | Townsend et al. |
| 7,279,011 B2 | 10/2007 | Phillips |
| 7,341,603 B2 | 3/2008 | Christensen |
| 7,347,877 B2 | 3/2008 | Clausen et al. |
| 7,419,509 B2 | 9/2008 | Christensen |
| 7,429,272 B2 | 9/2008 | Townsend et al. |
| 7,431,737 B2 | 10/2008 | Ragnarsdottir et al. |
| 7,462,201 B2 | 12/2008 | Christensen |
| 7,520,904 B2 | 4/2009 | Christensen |
| 7,531,006 B2 | 5/2009 | Clausen et al. |
| 7,572,299 B2 | 8/2009 | Christensen |
| 7,578,852 B2 | 8/2009 | Townsend et al. |
| 7,618,464 B2 | 11/2009 | Christensen |
| 7,637,659 B2 | 12/2009 | Liu et al. |
| 7,637,957 B2 | 12/2009 | Ragnarsdóttir et al. |
| 7,727,285 B2 | 6/2010 | Christensen et al. |
| 8,070,829 B2 | 12/2011 | Townsend et al. |
| 2002/0040249 A1 | 4/2002 | Phillips |
| 2002/0082713 A1 | 6/2002 | Townsend et al. |
| 2002/0087216 A1 | 7/2002 | Atkinson et al. |
| 2002/0116072 A1 | 8/2002 | Rubie et al. |
| 2002/0128727 A1 | 9/2002 | Merlette et al. |
| 2002/0143408 A1 | 10/2002 | Townsend et al. |
| 2002/0183860 A1 | 12/2002 | Wilkinson et al. |
| 2003/0045944 A1 | 3/2003 | Mosler et al. |
| 2003/0093158 A1 | 5/2003 | Phillips et al. |
| 2003/0120353 A1 | 6/2003 | Christensen |
| 2003/0191540 A1 | 10/2003 | Townsend et al. |
| 2004/0064195 A1 | 4/2004 | Herr |
| 2004/0068327 A1 | 4/2004 | Christensen |
| 2004/0122529 A1 | 6/2004 | Townsend et al. |
| 2004/0181289 A1 | 9/2004 | Bedard et al. |
| 2005/0033451 A1 | 2/2005 | Aigner et al. |
| 2005/0038524 A1 | 2/2005 | Jonsson et al. |
| 2005/0038525 A1 | 2/2005 | Doddroe et al. |
| 2005/0060045 A1 | 3/2005 | Smith et al. |
| 2005/0071018 A1 | 3/2005 | Phillips |
| 2005/0107889 A1 | 5/2005 | Bedard et al. |
| 2005/0137717 A1 | 6/2005 | Gramnäs et al. |
| 2005/0203640 A1 | 9/2005 | Christensen |
| 2005/0216097 A1 | 9/2005 | Rifkin |
| 2006/0069450 A1 | 3/2006 | McCarvill et al. |
| 2006/0167563 A1 | 7/2006 | Johnson et al. |
| 2006/0173555 A1 | 8/2006 | Harn et al. |
| 2006/0247794 A1 | 11/2006 | Doddroe et al. |
| 2007/0027557 A1 | 2/2007 | Jonsson et al. |
| 2007/0106395 A9 | 5/2007 | Clausen et al. |
| 2007/0213840 A1 | 9/2007 | Townsend et al. |
| 2008/0046096 A1 | 2/2008 | Bedard et al. |
| 2008/0188951 A1 | 8/2008 | Christensen et al. |
| 2009/0105845 A1 | 4/2009 | Curtis |
| 2009/0287315 A1 | 11/2009 | Lecomte et al. |
| 2009/0306792 A1 | 12/2009 | Lecomte et al. |
| 2010/0004757 A1 | 1/2010 | Clausen et al. |

FOREIGN PATENT DOCUMENTS

| WO | WO 02-051342 | 7/2002 |
|----|--------------|--------|
| WO | WO 2004/032809 | 4/2004 |
| WO | WO 2005/018495 | 3/2005 |

OTHER PUBLICATIONS

Össur Allurion® product; http://www.ossur.com/template1.asp-?pageid=84, last visited Dec. 15, 2003, and Product Catalog pp. 146-149; available before Aug. 15, 2003.

Össur Low Profile Re-Flex VSP® product; Össur Prosthetics Product Catalog, pp. 195-203, 2005.

Össur LP Vari-Flex® product; Össur Prosthetics Product Catalog, pp. 175-178, 2005.

Össur Modular III™ product; Össur Prosthetics Product Catalog, pp. 179-186, 2005.

Össur Re-Flex VSP® product; Össur Prosthetics Product Catalog, pp. 187-194, 2005.

Össur Vari-Flex® product; ÖOssur Prosthetics Product Catalog, pp. 167-174, 2005.

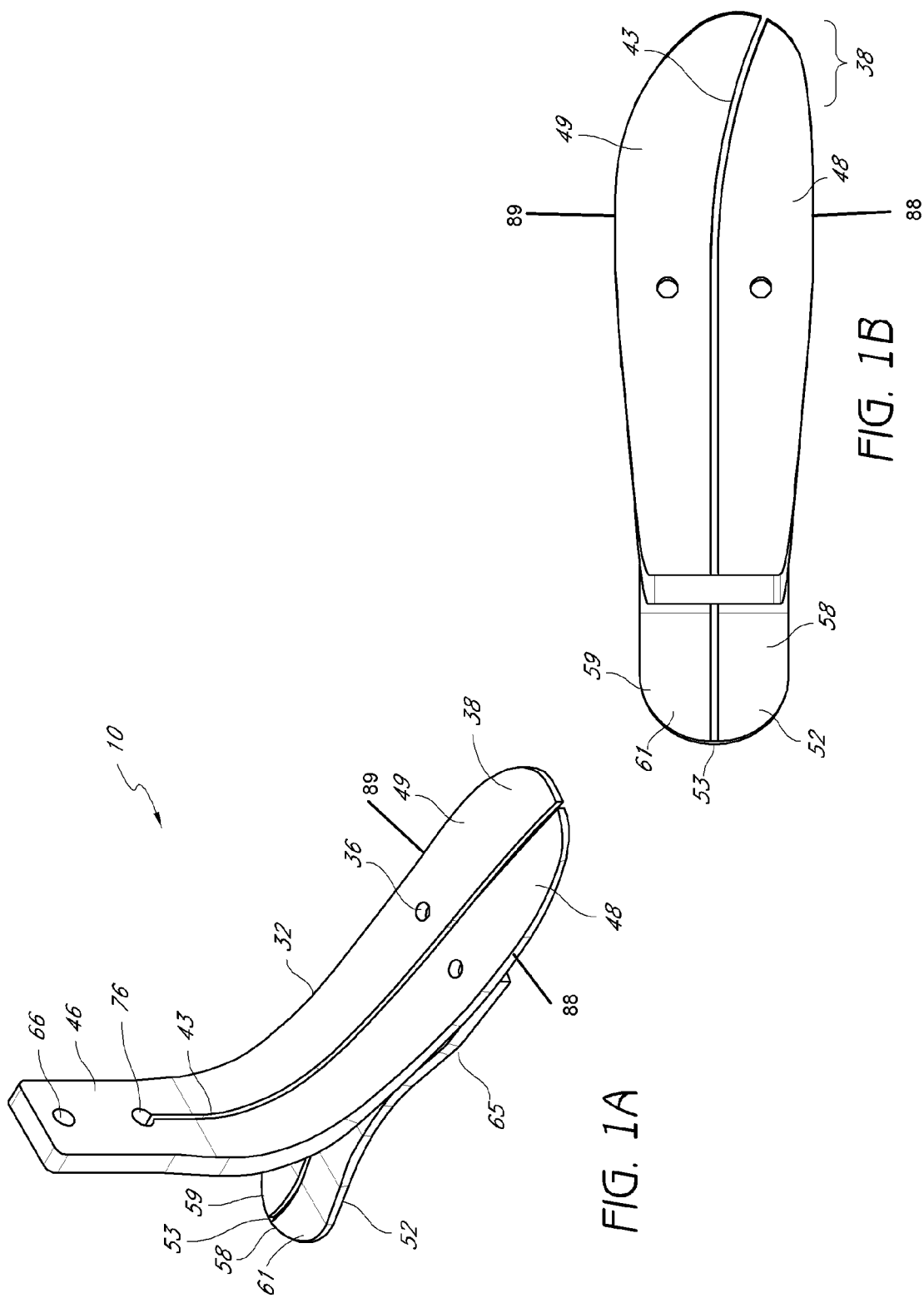

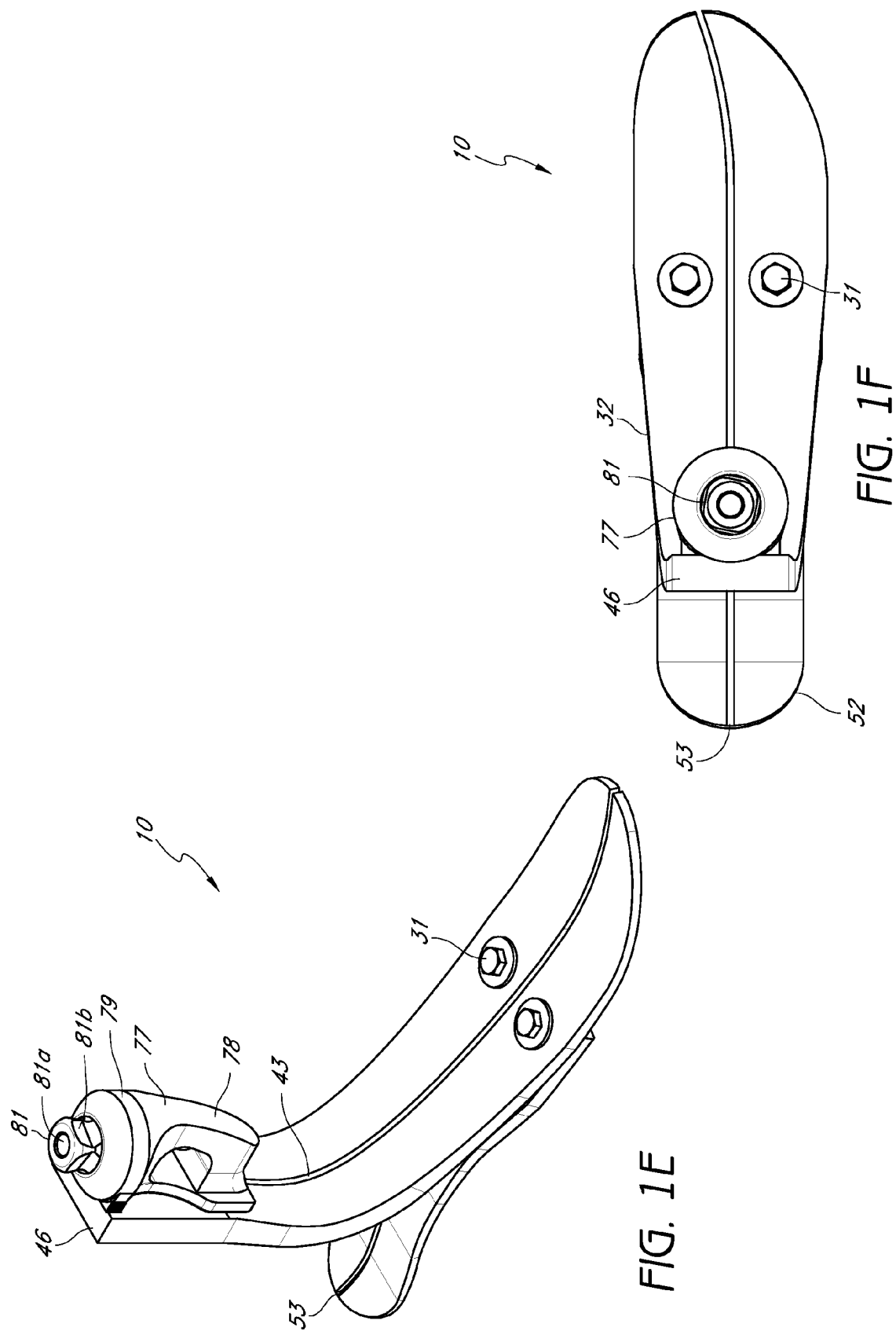

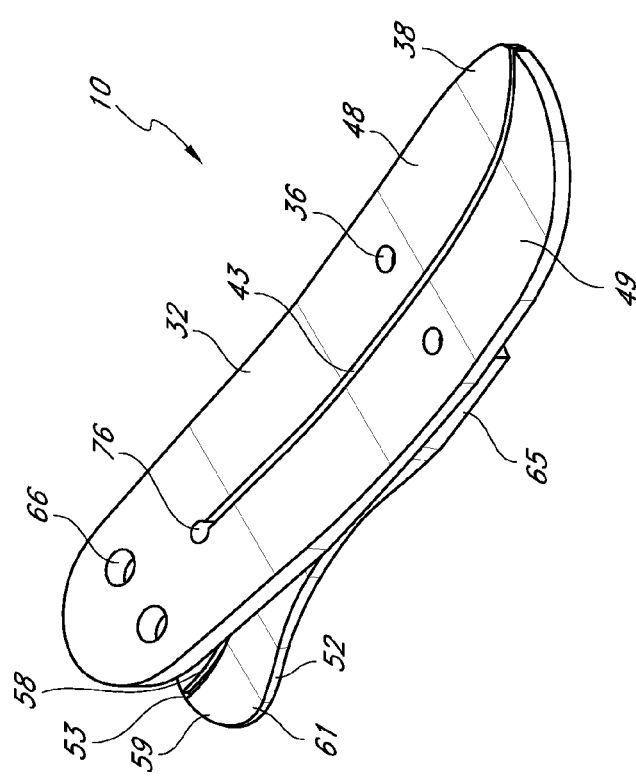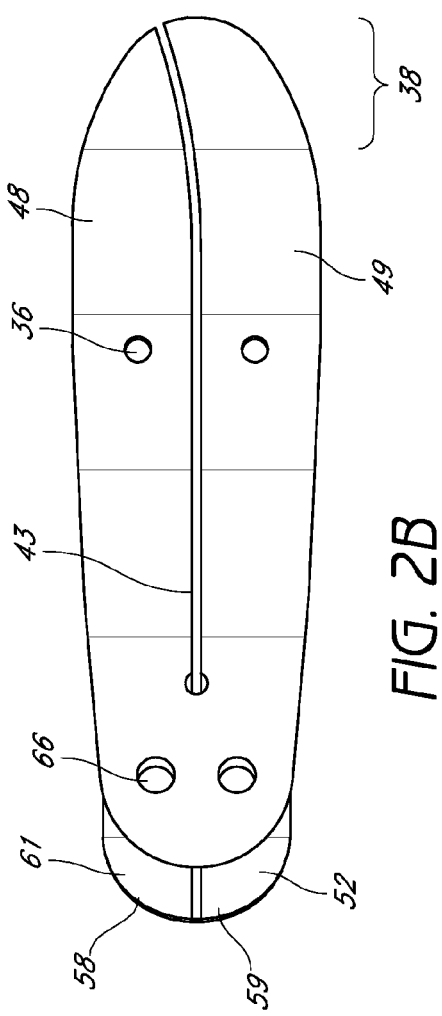

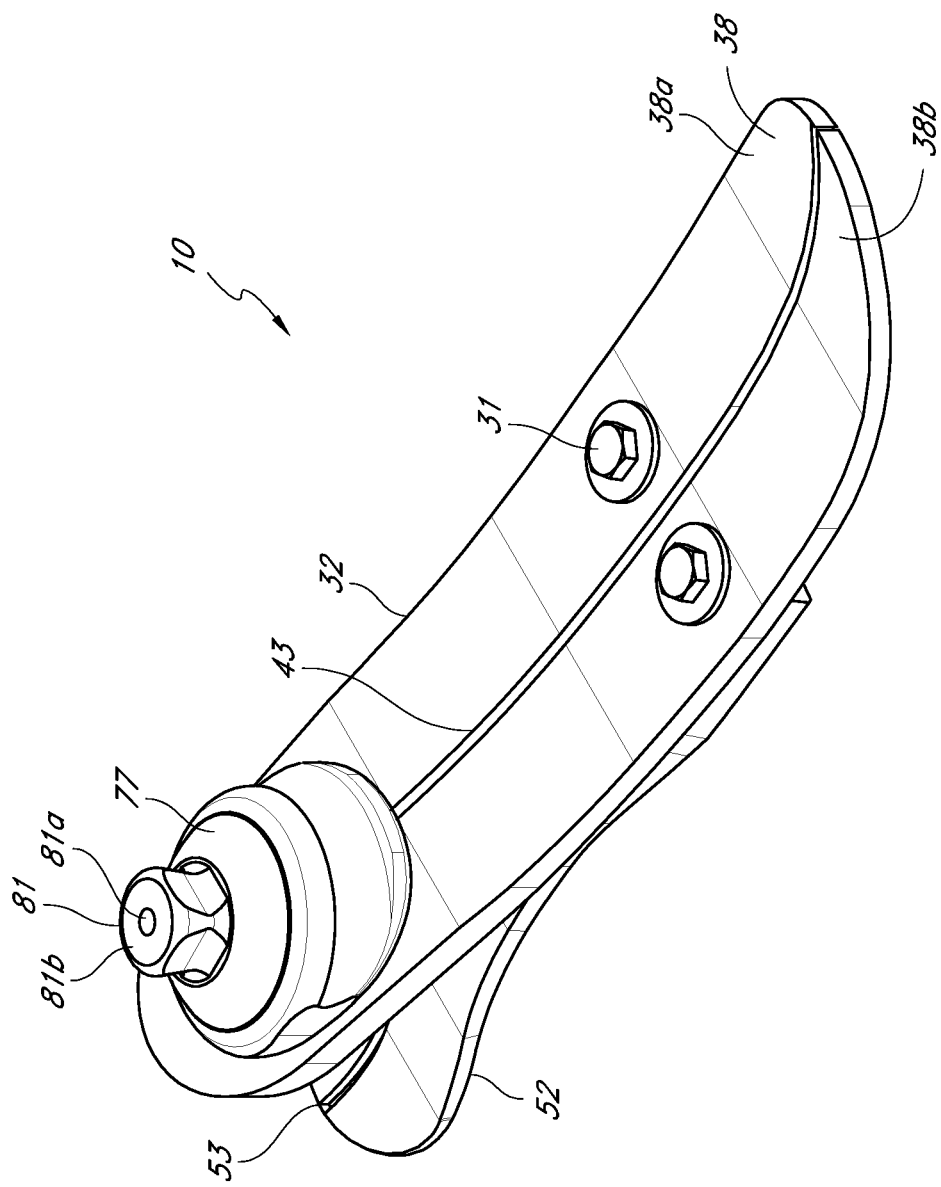

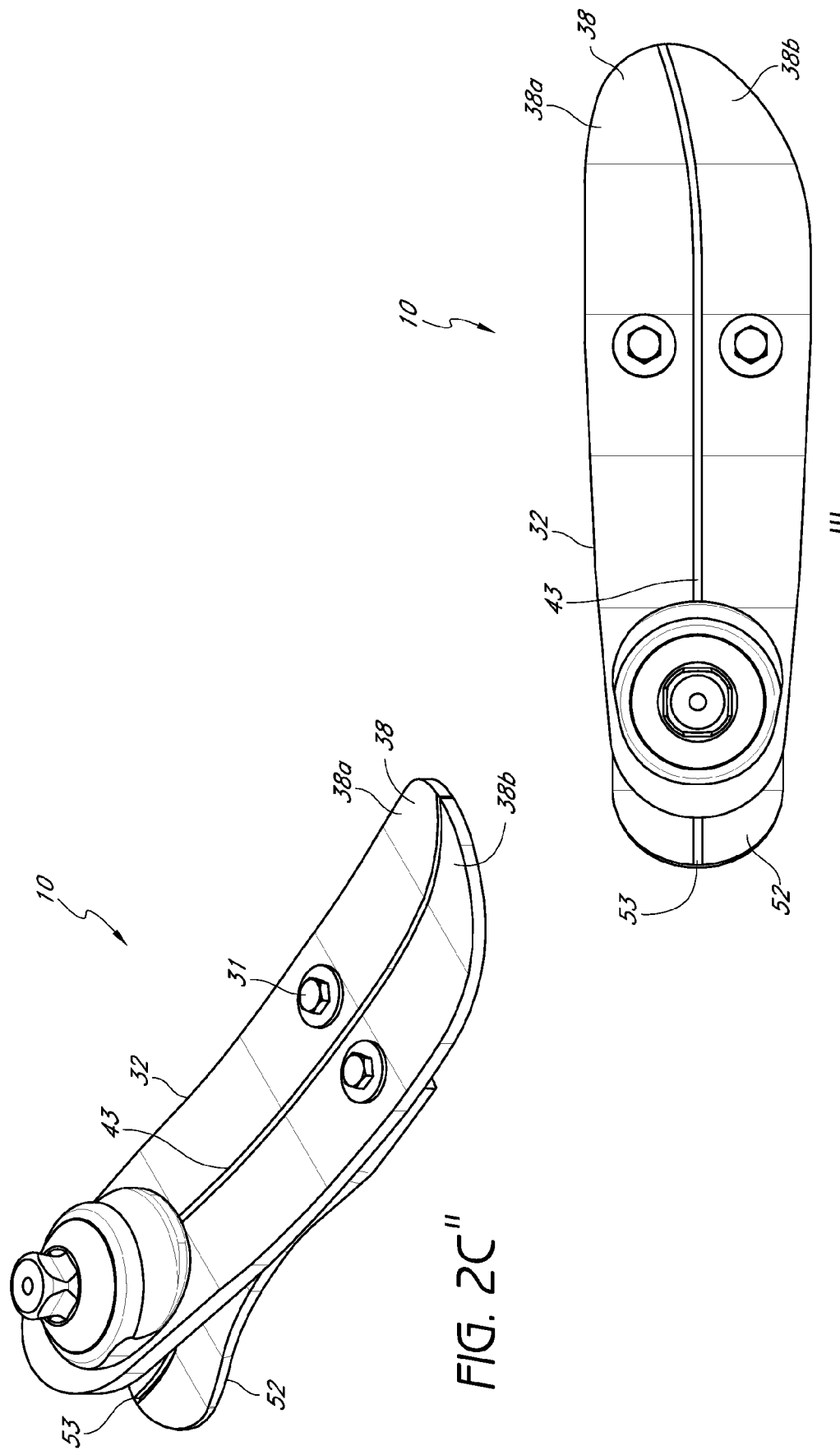

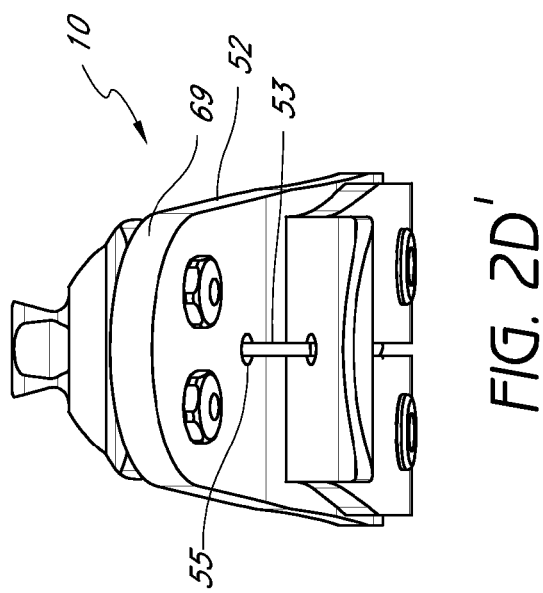
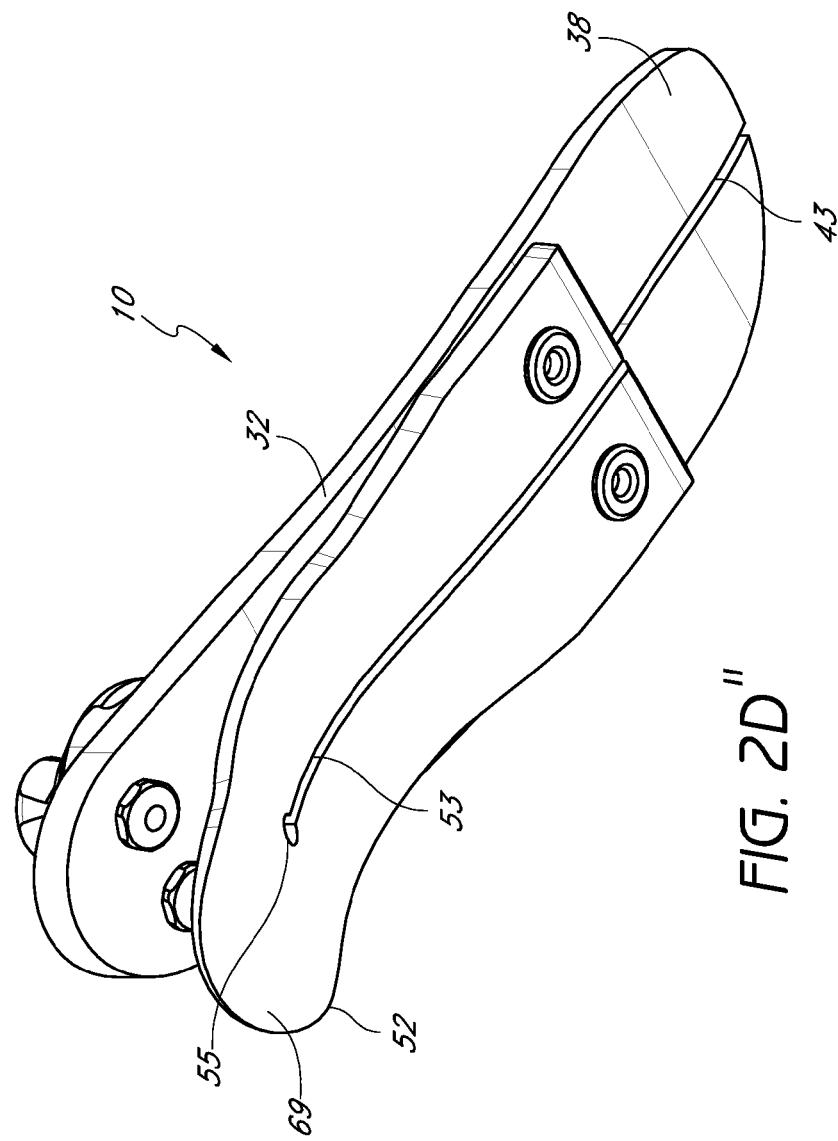
FIG. 2D'
FIG. 2D''

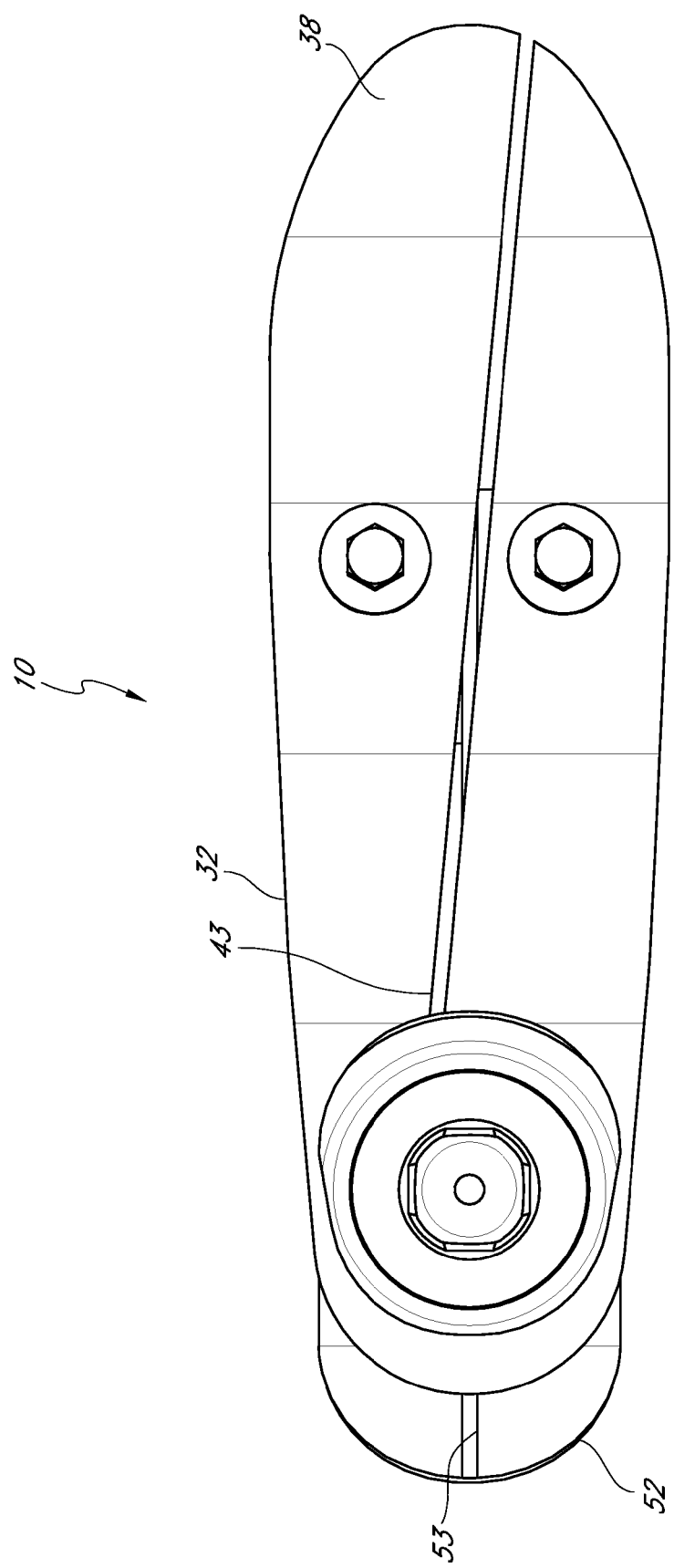

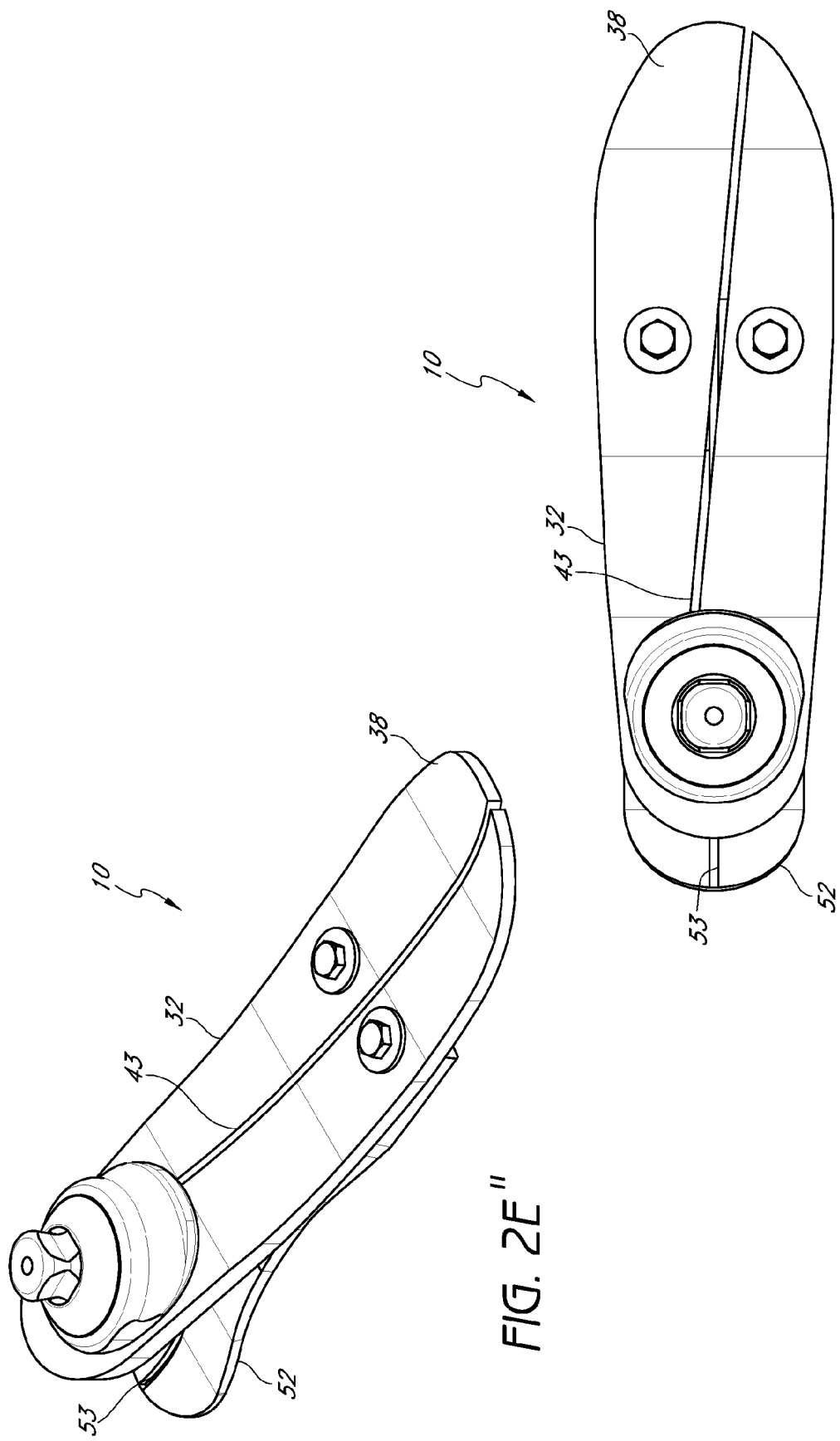

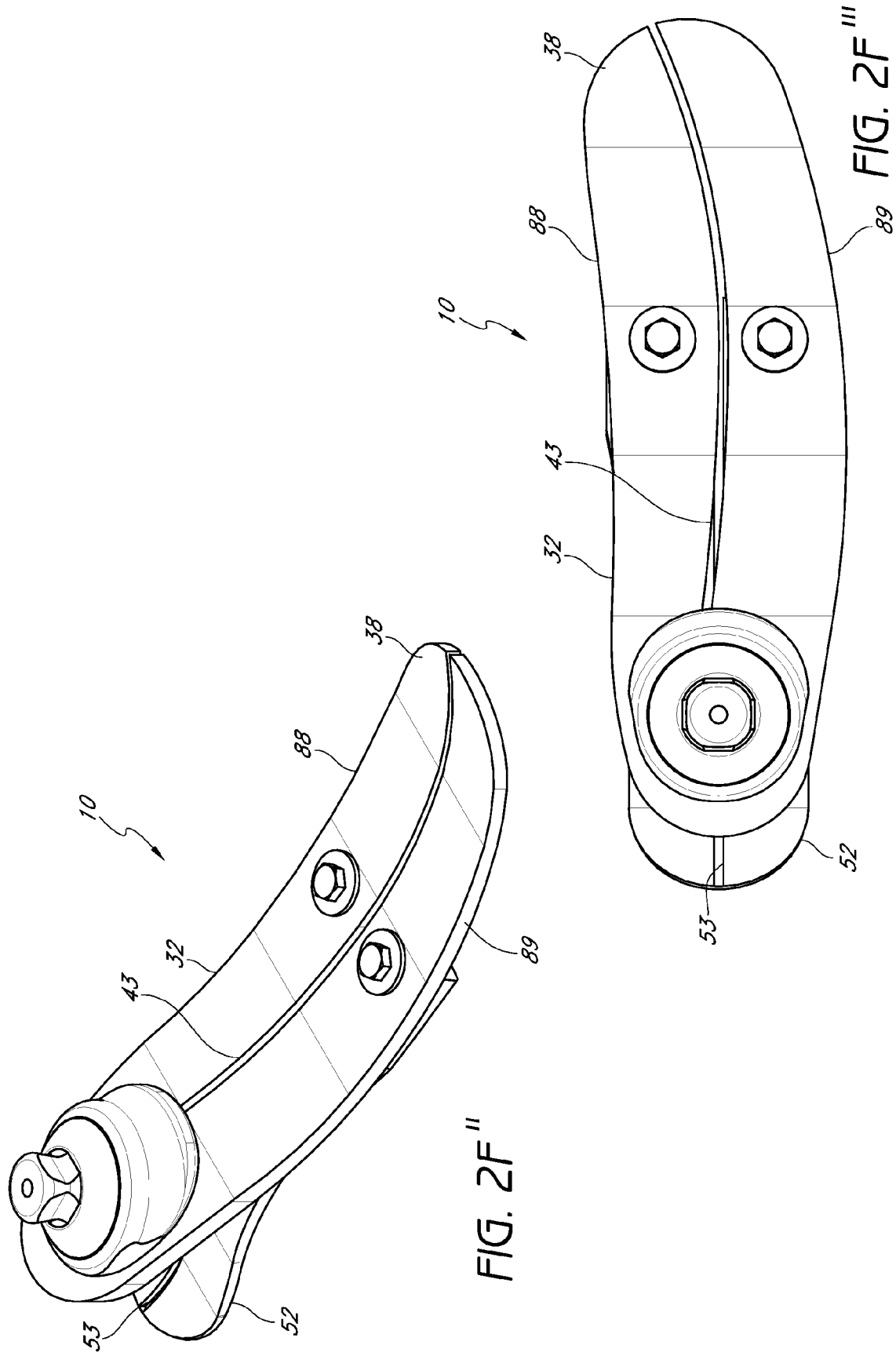

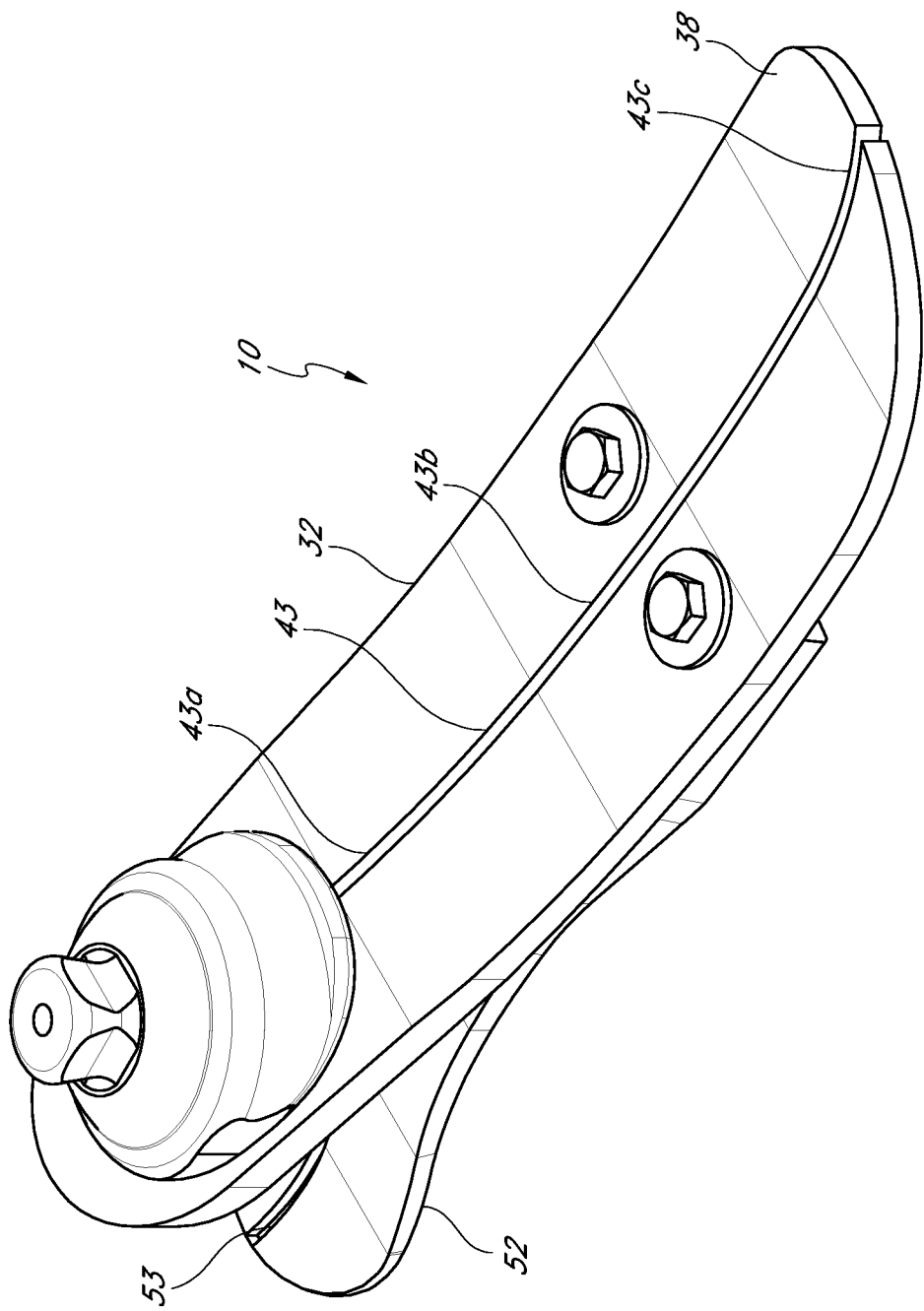

FIG. 2G''''

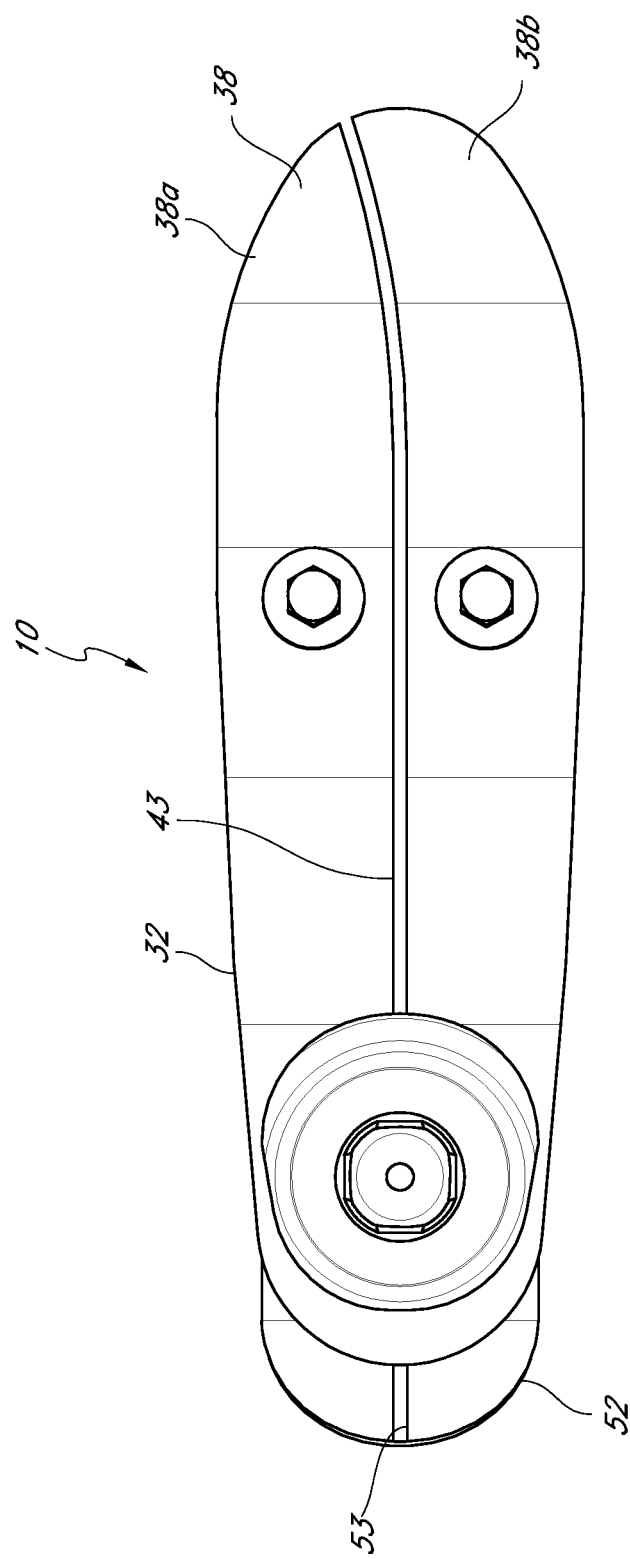
FIG. 2H"

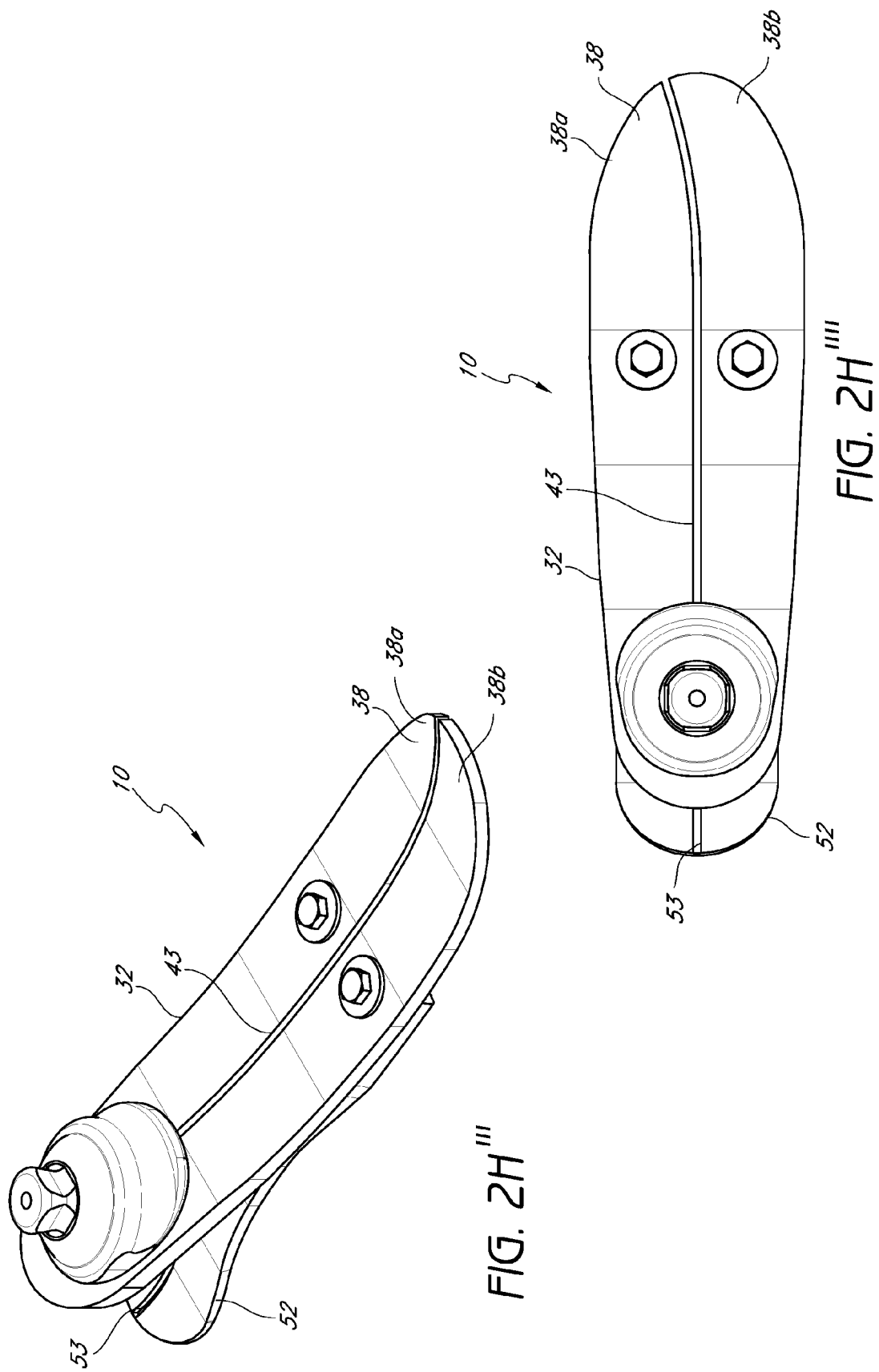

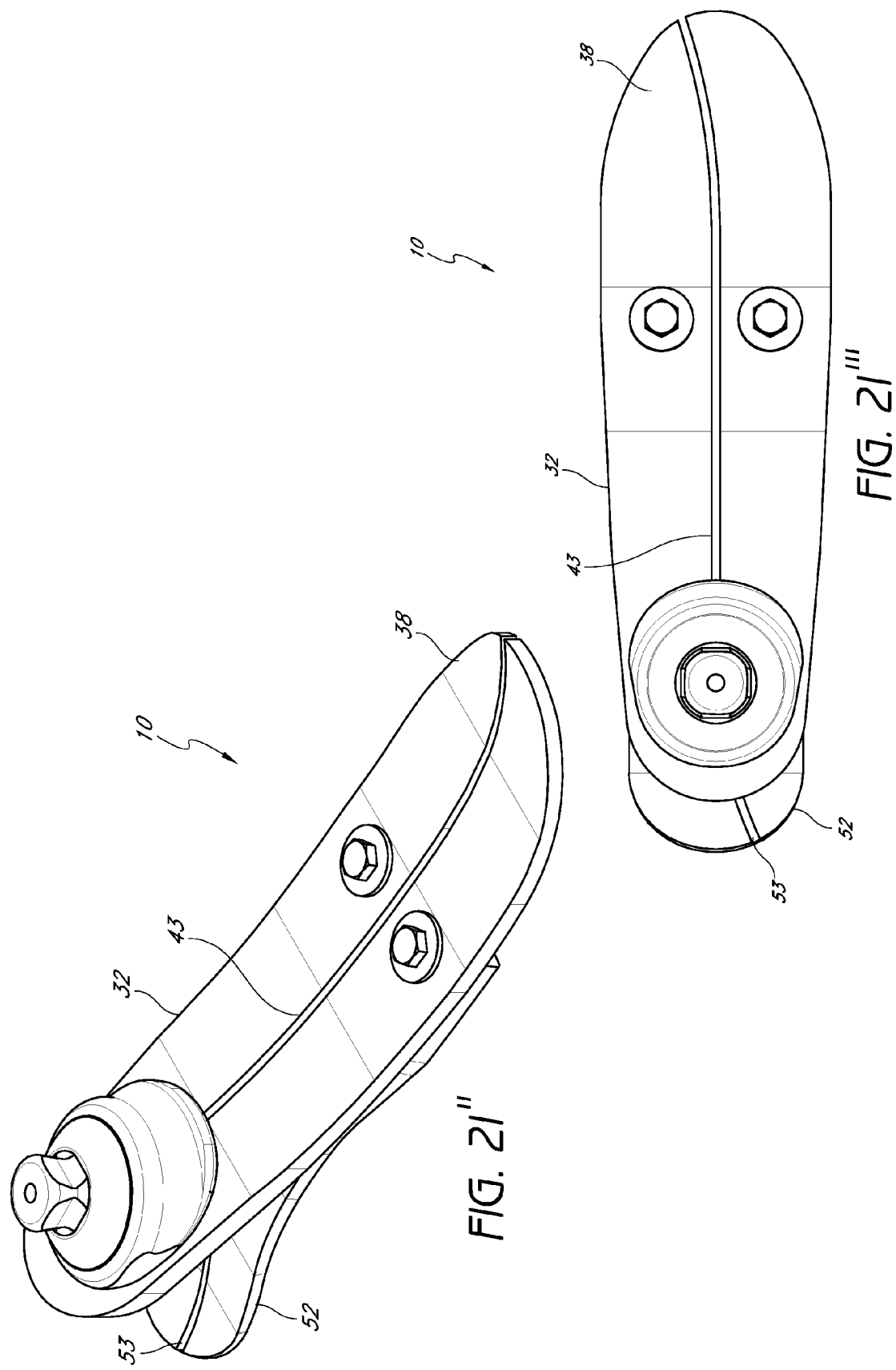

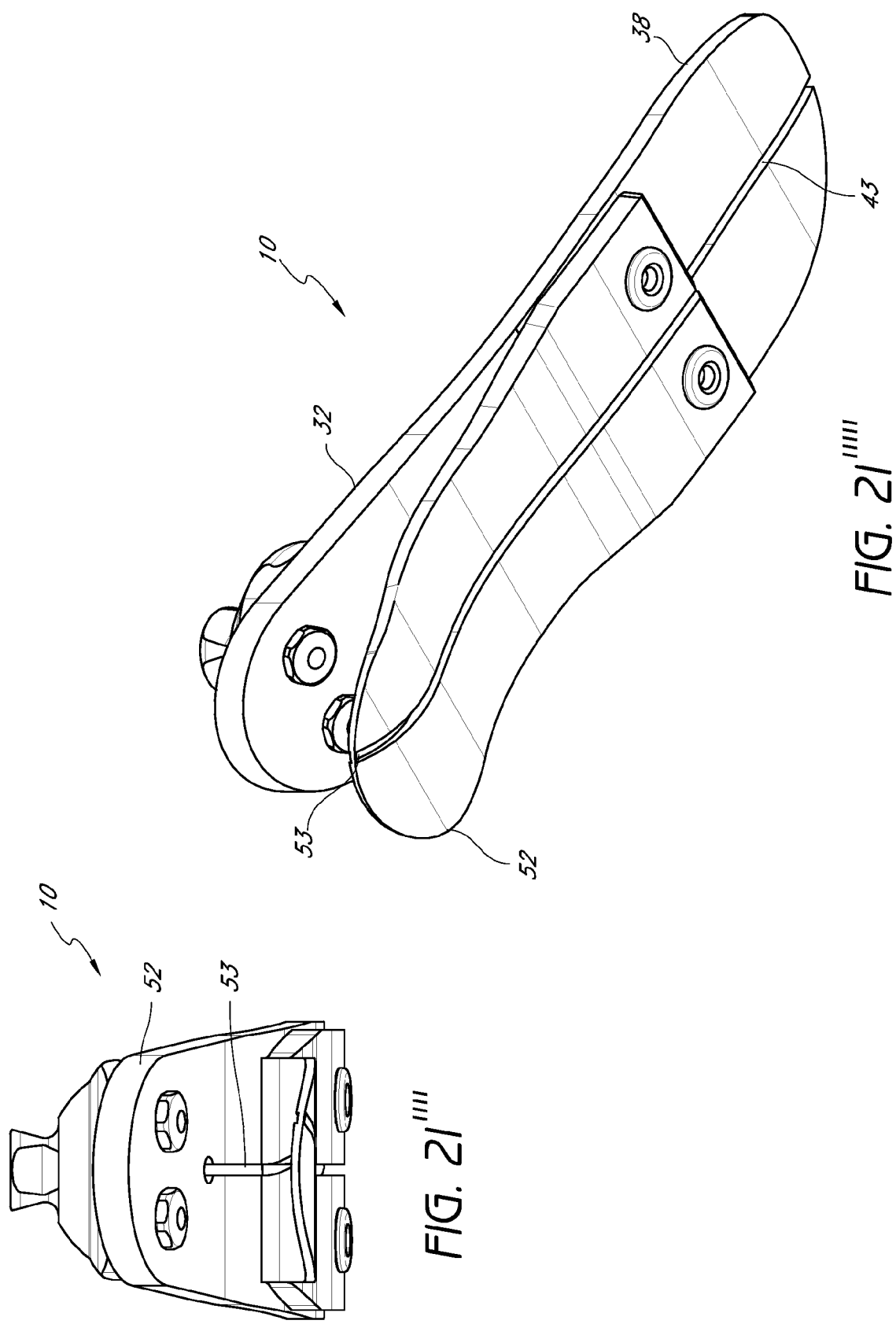

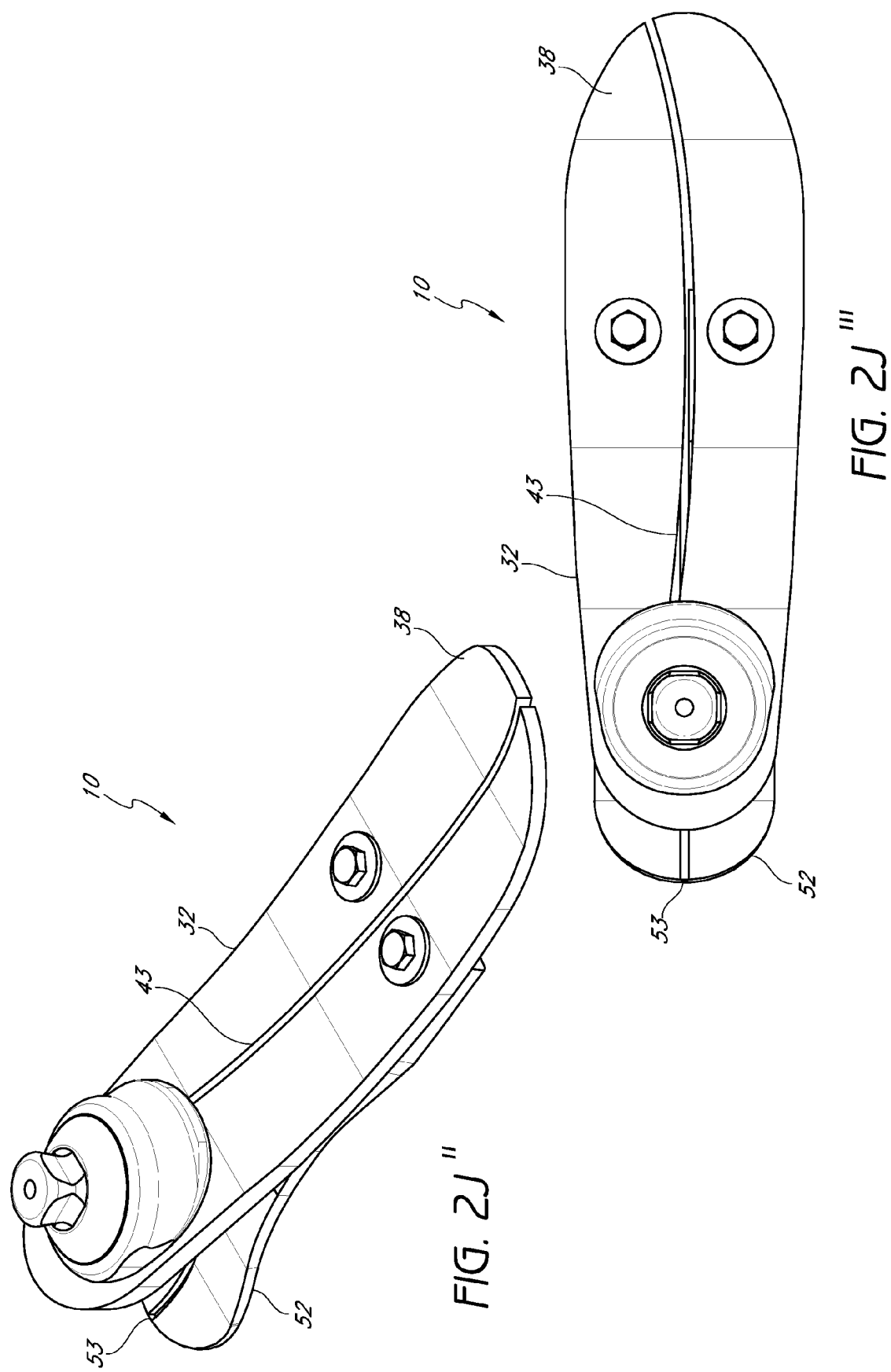

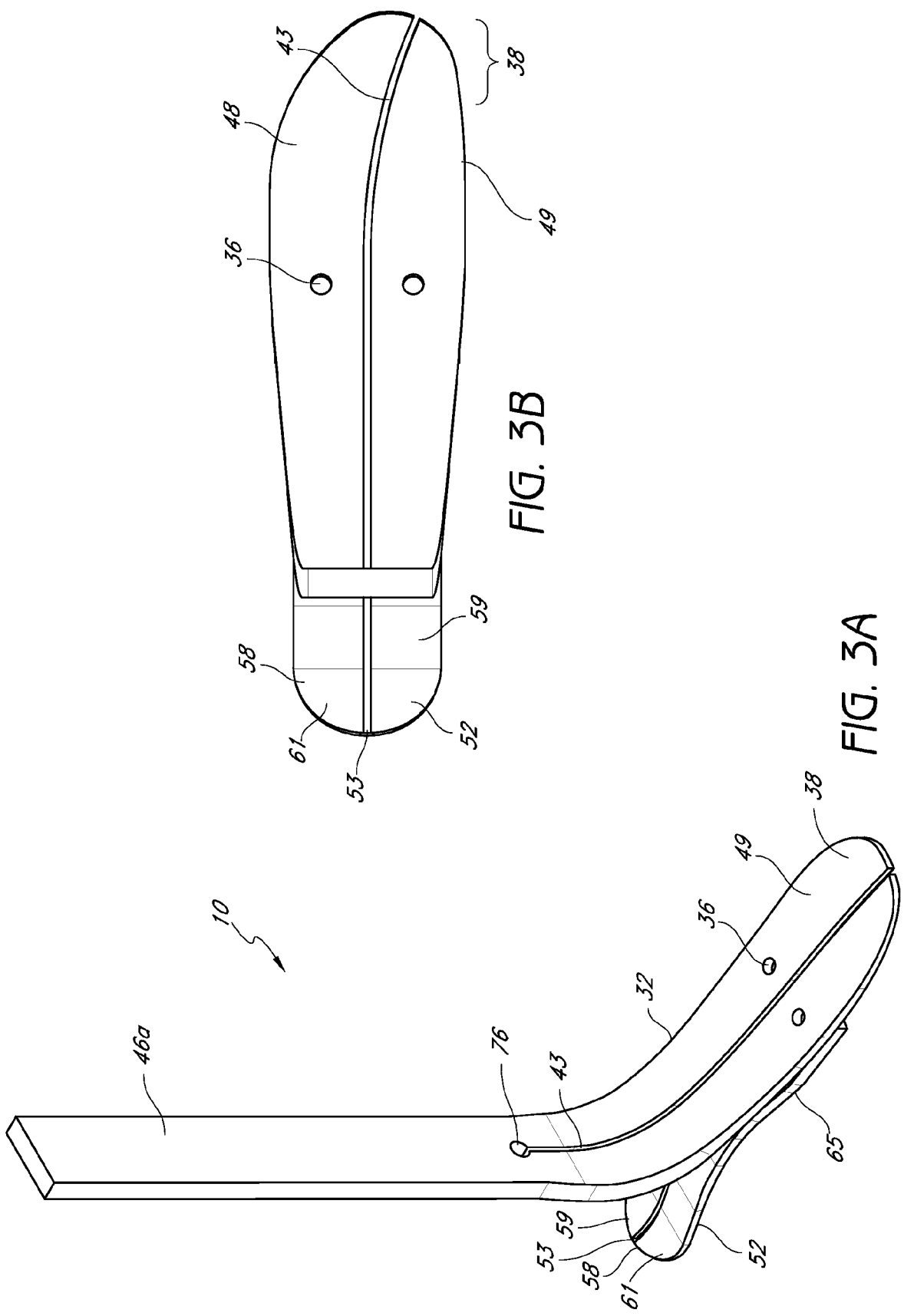

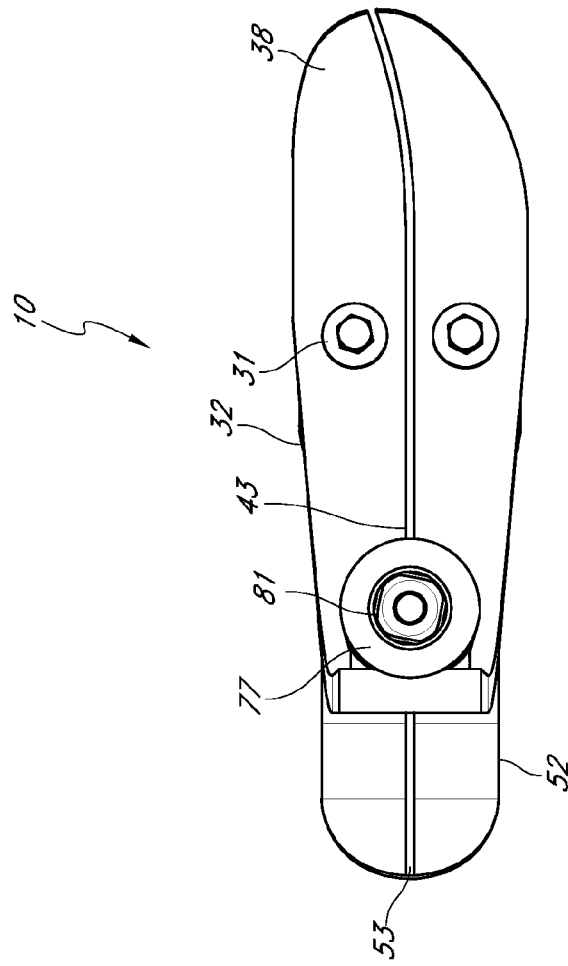
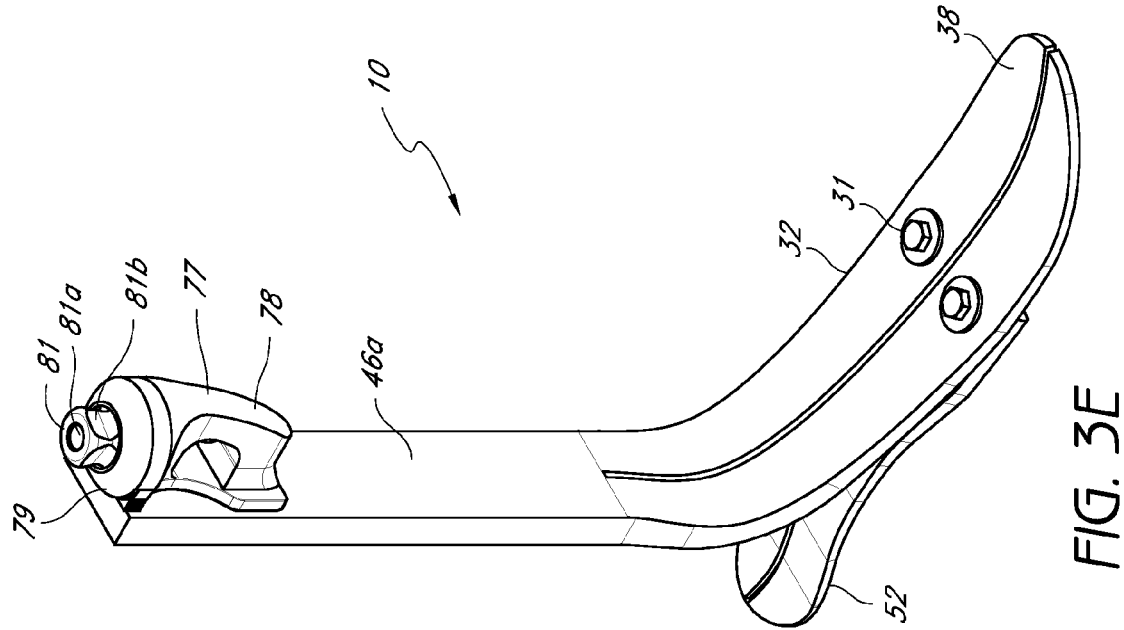

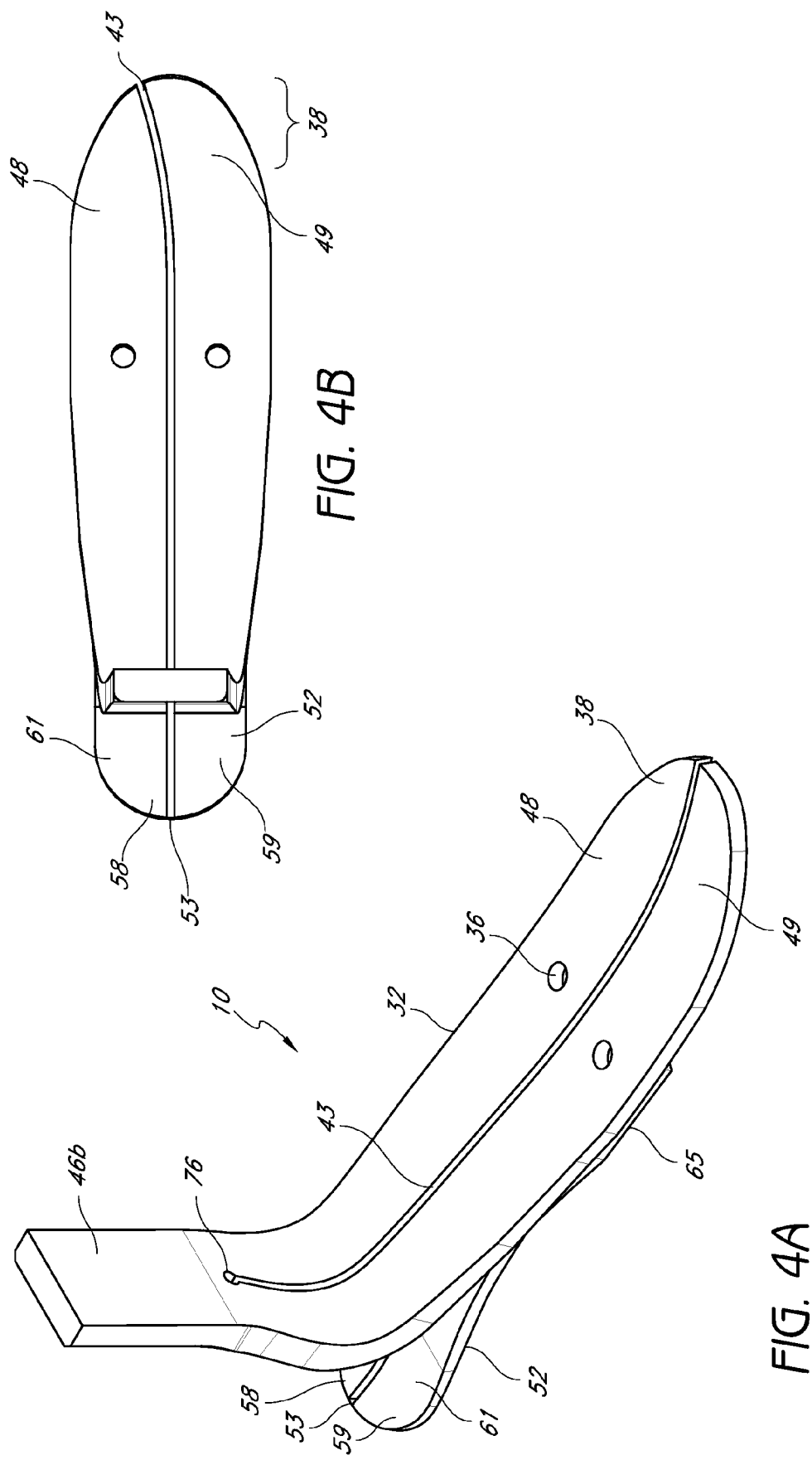

PROSTHETIC FOOT WITH A CURVED SPLIT

The present application claims priority under 35 U.S.C. §119(e) to U.S. Provisional Patent Application Ser. No. 61/308,818, entitled "PROSTHETIC FOOT WITH A CURVED SPLIT," filed Feb. 26, 2010. The entire disclosure of the priority application is hereby expressly incorporated by references in its entirety and should be considered a part of this specification.

BACKGROUND OF THE INVENTION

1. Field of the Invention

The present application relates in certain embodiments to prosthetic feet. In particular, the present application in certain embodiments relates to prosthetic feet with a curved split.

2. Description of the Related Art

Split foot prostheses are known in the art, for example in U.S. Pat. No. 6,071,313, which describes a prosthetic foot characterized by an ankle portion and a foot portion secured to one another. The foot portion and ankle portion are bifurcated into multiple side-by-side foot portions by the provision of a slot in the foot and ankle portions such that they are capable of movement independent from one another.

SUMMARY OF THE INVENTION

Prosthetic feet having a split feature are described. In one embodiment, a prosthetic foot comprises a plate-like upper element having an upper section at a posterior end of the upper element, wherein the upper element extends downward and forward from the upper section to a toe section at an anterior end of the upper element. The upper element includes an upper split that separates the upper element into an upper medial blade and an upper lateral blade. The upper element extends from an opening in the upper element spaced from the posterior end of the upper element to the anterior end of the upper element, and includes a portion that is substantially straight followed by a portion that curves in a medial or lateral direction. The length of the curved portion of the upper split is between about $1/10$ and $1/4$ of the total length of the upper split, though the length of the split can be longer. The prosthetic foot further comprises a plate-like lower element connected to the upper element, the lower element including a heel section at a posterior end of the lower element and a front section at an anterior end of the lower element. The lower element includes a lower split that separates the lower element into a lower medial blade and a lower lateral blade, the lower split extending from a posterior end to the anterior end of the lower element.

In another embodiment, a prosthetic foot comprises a plate-like upper element having an upper section at a posterior end of the upper element, the upper element extending downward and forward from the upper section to a toe section at an anterior end of the upper element. The upper element includes an upper split that separates the upper element into an upper medial blade and an upper lateral blade, wherein the upper split extends from a location spaced from the posterior end of the upper element to the anterior end of the upper element. The prosthetic foot further includes a plate-like lower element connected to the upper element, the lower element including a heel section at a posterior end of the lower element and a front section at an anterior end of the lower element. The lower element includes a lower split that separates the lower element into a lower medial blade and a lower lateral blade, the lower split extending from a posterior end toward the anterior end of the lower element. At least one of the upper split and the lower split includes a portion that curves in a medial or lateral direction. In another embodiment, at least one of the upper split and the lower split includes a portion that is non-parallel relative to a longitudinal axis of the upper element or the lower element.

BRIEF DESCRIPTION OF THE DRAWINGS

FIGS. 1A-1F illustrate different views and features of a first foot prosthesis having one or more splits according to embodiments of the present application.

FIGS. 2A-2J''' illustrate different views and features of a second foot prosthesis having one or more splits according to embodiments of the present application.

FIGS. 3A-3F illustrate different views and features of a third foot prosthesis having one or more splits according to embodiments of the present application.

FIGS. 4A-4B illustrate different views and features of a fourth foot prosthesis having one or more splits according to embodiments of the present application.

DETAILED DESCRIPTION OF THE EMBODIMENTS

Improved prosthetic feet are described that are capable of providing multi-axial movement capabilities of a natural human foot. In particular, the prosthetic feet described herein include one or more splits that are designed to provide enhanced roll-over properties while in use. The splits described herein can have one or more sections that curve in a lateral or medial direction to assist in roll-over of the prosthetic foot. However, splits that may not be curved that can nevertheless provide enhanced roll-over properties are also described below.

Figure 1C:
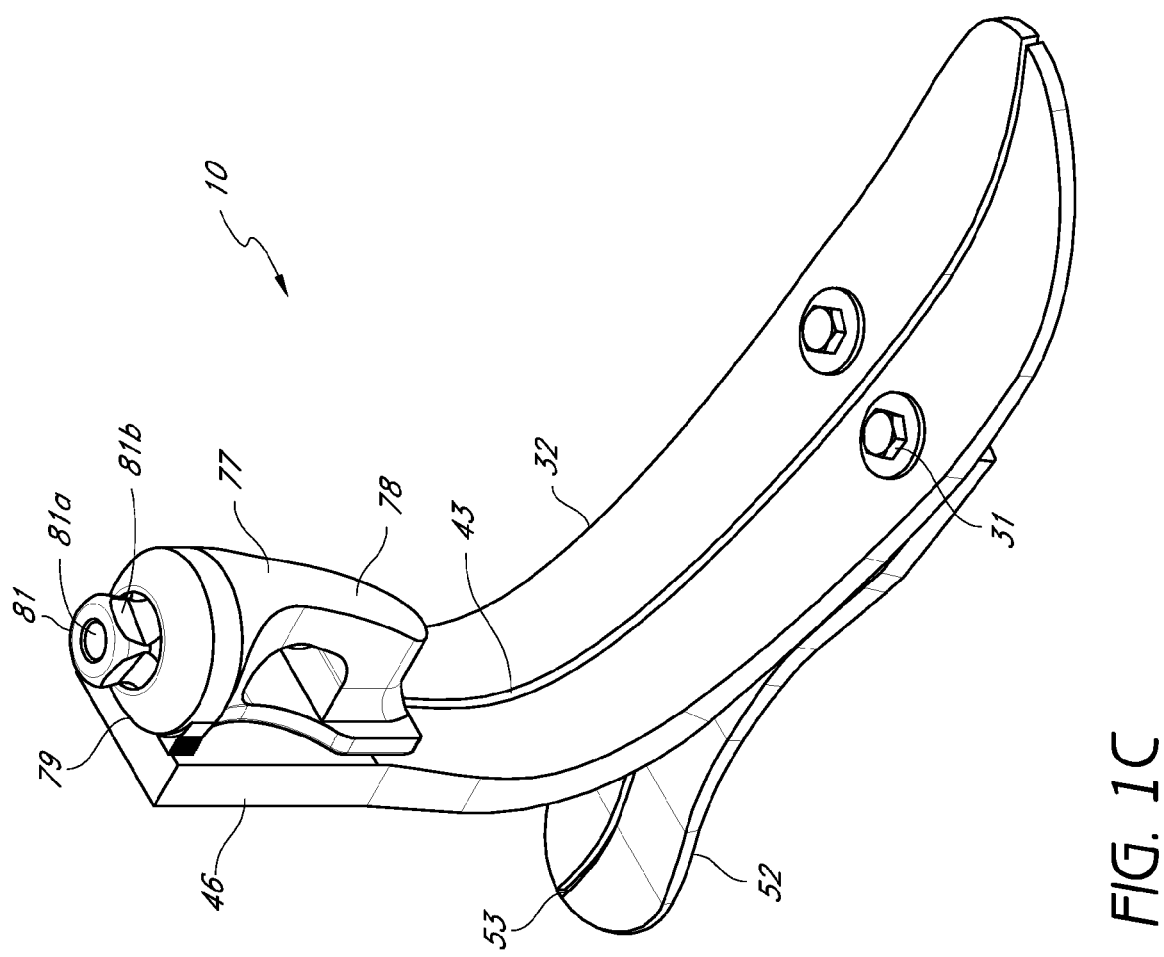
Figure 1D:
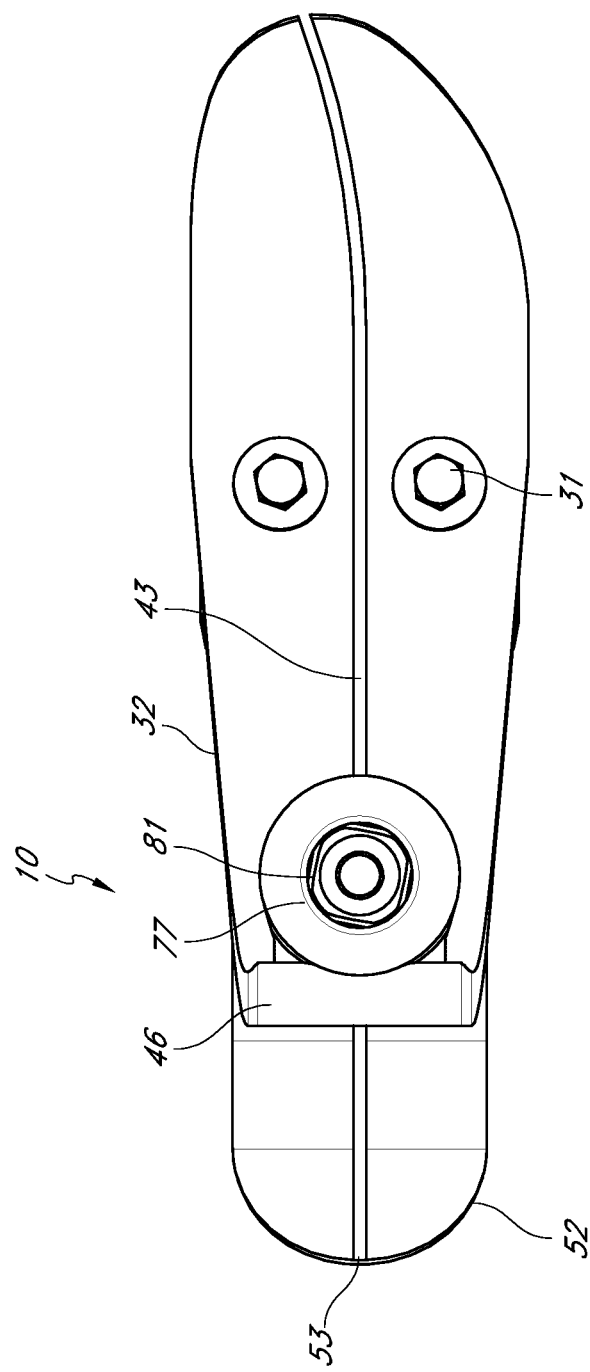

FIGS. 1A-1F illustrate different views and features of a first foot prosthesis having one or more splits (preferably curved) according to embodiments of the present application. FIGS. 1A and 1B illustrate one embodiment of a prosthetic foot 10 with a curved split. The prosthetic foot 10 includes an upper element 32 and a lower element 52. The upper element 32 includes a plate-like body having a curved split 43 that separates the upper element 32 into an upper medial blade 48 having a medial edge 88 and an upper lateral blade 49 having a lateral edge 89. The upper element 32 further includes a toe section 38 at its anterior end, lower attachment holes 36 in an arch portion of the upper element, and an upper section 46 at the posterior end that includes upper attachment hole 66 and hole or opening 76 spaced a distance away from the posterior end. The lower element 52 includes a plate-like body having split 53 that separates the lower element 52 into a lower medial blade 58 and a lower lateral blade 59. The lower element 52 includes a heel section 61 at its posterior end and a front section 65 at its anterior end with an arch section located therebetween. As shown in FIG. 1A, the anterior end of the upper element 32 terminates anterior to the anterior end of the lower element 52.

The upper element 32 of the prosthetic foot includes a plate-like body having an upper section 46 with an attachment hole 66. In some embodiments, the upper element 32 is vertical or substantially vertical and has a substantially rectangular transverse cross-section along its length. In some embodiments, the upper section 46 serves as an ankle member that is substantially rigid and capable of sustaining torsional, impact and other applied loads. In some embodiments, the upper section 46 is formed continuously with the upper element 32 as a unitary piece, while in other embodiments, the upper portion 46 is formed separately from the rest of the upper element 32. The attachment hole 66 on the upper portion 46 can serve as a connection point to structures attachable to the upper element 32, such as adapters and pylons for prosthetic limbs. In one embodiment the attachment hole 66 is configured to connect the upper element to an attachment adapter such as a male pyramid adapter (not shown).

From the upper portion 46 of the prosthetic foot, the upper element 32 curves substantially downward and forward and forms a toe section 38, located near an anterior end of the upper element 32. Preferably, the toe section 38 of the upper element 32 is curved upwardly, such as at an angle between 5 and 45 degrees relative to a walking surface. This upward curvature can provide the toe section 38 with a more natural feeling when walking over uneven surfaces and also helps to provide easier rollover capabilities.

Upper split 43 separates the plate-like body of the upper element 32 into an upper medial blade 48 and an upper lateral blade 49. The split 43 begins at the hole 76, which in some embodiments, is located between about ⅓ to ¾ of the distance down from the top of the upper portion 46. The hole 76 is provided to prevent undesired excessive loading and stress concentrations at this region, although in some embodiments, it can also serve as an attachment hole. From hole 76, the split 43 travels down towards the toe section 38. As shown in FIG. 1A, the split can begin at hole 76 and travel down to an anterior edge of the toe section 38, thereby advantageously providing multi-axial capabilities along a majority of the length of the upper element 32. In other embodiments, the split 43 need not extend from the upper portion 46 of the prosthetic foot and can instead be of a length shorter than that shown in FIG. 1A.

While in some embodiments, the split 43 is substantially straight throughout its entire length, in a preferred embodiment, the split 43 curves in either a medial or lateral direction. For example, as shown in FIGS. 1A and 1B, from a posterior to anterior direction, the split 43 is substantially straight from the hole or opening 76 downward past the lower attachment holes 36. The split 43 then curves medially until it meets the anterior edge of the upper element 32. The benefit of the curve, which can be medial or lateral, is that it provides smoother more natural rollover properties relative to prosthetic feet having splits without curves. In some embodiments, the curved portion of the split 43 comprises between about ⅒ to ¾ of the overall length of the split, or between about ⅒ to ¼ of the overall length of the split. This latter range can be particularly advantageous for providing enhanced rollover on selected portions of the prosthetic foot, such as near the toe region. In some embodiments, the curved portion can comprise even greater than ¾ of the overall length of the split 43, and in some cases, the split 43 can be curved along its entire length. In some embodiments, the curved portion of the split 43 comprises a length between about 10 and 90 mm. These proportions and dimensions are also applicable to the split 53 on the lower element 52, which can also be curved in some embodiments. As shown in FIGS. 1A and 1B, the split 43 can be a single continuous split that extends along a majority of a longitudinal length of the upper element 32.

In some embodiments, at least a portion of the split 43 is located along a longitudinal axis of the upper element 32 that is substantially centered such that the widths of the upper medial blade 48 and upper lateral blade 49 are substantially similar. In other embodiments, at least a portion of the split 43 is off-center such that the widths of the upper medial blade 48 and upper lateral blade 49 are noticeably different.

The upper element 32 can be operatively connected to the lower element 52. In some embodiments, the upper element 32 is connected to the lower element 52 by using mechanical screws or bolts 31 placed in the lower attachment holes 36, while in other elements, adhesives may be used. Direct casting or molding can also be used to connect the upper element 32 with the lower element 52. In some embodiments, the upper element 32 and the lower element 52 are permanently fixed with each other, while in other embodiments, the two elements can be separated to provide for adjustability depending on the user's needs. The upper element 32 and the lower element 52 can serve as two independent members capable of flexing substantially independently of each other, advantageously providing increased stability.

Lower element 52 comprises a posterior region, or heel section 61 at the posterior end, and an anterior region, or front section 65 at the anterior end. The front section 65 of the lower element 52 is attached to a bottom surface of upper element 32. In some embodiments, the lower element 52 has substantially the same width on average as the upper element 32, while in other embodiments, the average width may differ (e.g., the average width of the lower element 52 may be smaller than the average width of the upper element 32).

The lower element 52 includes a curved plate-like body with a substantially rectangular transverse cross-section that includes a concave downward region between the heel section 61 and front section 65 that approximates an arch portion of a human sole. The heel section 61 is upwardly curved toward the posterior end and helps to ensure that the heel section 61 does not strike the ground along a posterior edge of the heel. Instead, a portion of the heel section 61 forward of the posterior edge strikes the ground during heel strike. This portion has a greater surface area than the posterior edge. Thus, at heel strike, the lower element 52 is more stable because more of it is in contact with the ground. In some embodiments, the heel section 61 can extend posteriorly beyond the rear end of the upper element 32.

In one embodiment, lower split 53 extends from heel section 61 to front section 65 through the concave arch portion of the lower element 52. The split 53 separates a lower medial blade 58 from a lower lateral blade 59. The split 53 in the heel region 60 helps the heel section 61 to conform to uneven ground, which helps to stabilize the foot during heel strike. For example, the lower medial blade 58 may strike a pebble, while the lower lateral blade 59 strikes flat ground. In such a situation, the separate lower medial and lateral blades move independently of one another to conform to the uneven ground. The lower medial blade 58 can deflect a greater amount than the lower lateral blade 59 does in this situation. The pebble thus does not place as great a torque on the lower element 52 as it otherwise would in the absence of the split 53.

In some embodiments, the split 53 is located along a longitudinal axis of the lower element 52 that is substantially centered such that the widths of the lower medial blade 58 and lower lateral blade 59 are substantially similar. In other embodiments, the split 53 is off-center such that the widths of the lower medial blade 58 and lower lateral blade 59 are noticeably different. In addition, like the split 43 in the upper element 32, the split 53 can also include one or more medial or lateral curves, and may only extend partially along the length of the lower element.

In some embodiments, the split 53 in the lower element 52 is substantially aligned with portions of the split 43 in the upper element 32. In other embodiments, the split 53 in the lower element 52 is not aligned with the split 43 in the upper element 32. By providing splits 43 and 53 with independent alignments, the prosthetic foot 10 can more naturally replicate the natural functions of the human foot. For example, while split 53 in the lower element 52 can be substantially centered, split 43 in the upper element 32 can be off-centered such that a width of the upper medial blade 48 is greater than a width of the upper lateral blade 49 to more accurately represent a large toe member of a human foot and provide a more natural toe off. In addition, while split 53 in the lower element 52 can be substantially straight throughout its entire length, split 43 in the upper element 32 can be partially split and partially curved. By providing a split 43 in the upper element 32 and a separate split 53 in the lower element 52, the prosthetic foot 10 is suitable for use on a variety of different terrain, including uneven surfaces (e.g., rock surfaces) that may require flexing of both the toe and heel. In some embodiments, the split 53 in the lower element and/or the split 43 in the upper element can be filled in whole or in part with a resilient compressible material.

In some embodiments, the upper element 32 and lower element 52 can both be constructed of a strong, resilient material that is capable of flexing in multiple directions, particularly during motion from heel-strike through toe-off. The material can comprise multiple layers, or laminate. Examples of possible materials for upper element 32 and lower element 52 are carbon, any polymer material, and any composite of polymer or fiber. The polymer can be thermoset or thermoplastic. In a composite, the fiber reinforcement can be any type of fiber or filament, such as carbon, glass or aramid. The fibers can be long and unidirectional, or they can be chopped and randomly oriented. Other filaments, composed of, for example, synthetic aramid fibers (e.g., Kevlar) or nylon, can also be used to ensure lightweight and structurally dynamic characteristics. As illustrated in one embodiment, the upper and/or lower elements remain substantially unsecured to any other members other than each other or the attachment adapter, such that the upper and lower elements are capable of substantially unconstrained flexing along each of their lengths.

FIGS. 1C-1F illustrate additional embodiments of the first foot prosthesis according to embodiments of the present application. The prosthetic foot 10 includes an upper element 32 and a lower element 52. The upper element 32 includes a curved split 43 that separates the upper element into an upper medial blade and an upper lateral blade, while the lower element 52 includes a split 53 that separates the lower element 52 into a lower medial blade and a lower lateral blade. An adapter member 77 is operably connected to an upper section 46 of the upper element 32 via one or more upper attachment holes (not shown). Fasteners 31 are inserted through lower attachment holes 36 to attach the upper member 32 to the lower member 52.

As shown in FIGS. 1C-1F, the adapter member 77 includes a lower portion 78 and an upper portion 79. The lower portion 78 of the adapter member 77 is operably connected to the upper section 46 of the upper element 32. The upper portion 79 comprises a male pyramid 81 adapted to connect to a pylon or other prosthesis (not shown). The pyramid 81 has a generally flat top surface 81a and at least one side surface 81b. In the illustrated embodiments, the side surface 81b comprises four generally flat faces inclined relative to a longitudinal axis through the flat top surface 81a. However, one skilled in the art will appreciate that other shapes and surfaces can be provided for the adapter member 77, so long as it serves to connect the prosthetic foot 10 to a pylon or other prosthesis. In some embodiments, the adapter member 77 is removably connected to the upper element 32, while in other embodiments, the adapter member 77 is permanently attached to the upper element 32 of the prosthetic foot 10. In some embodiments, at least a portion of the curved split 43 of the upper element 32 extends under a surface of the adapter member 77.

Figure 2C:
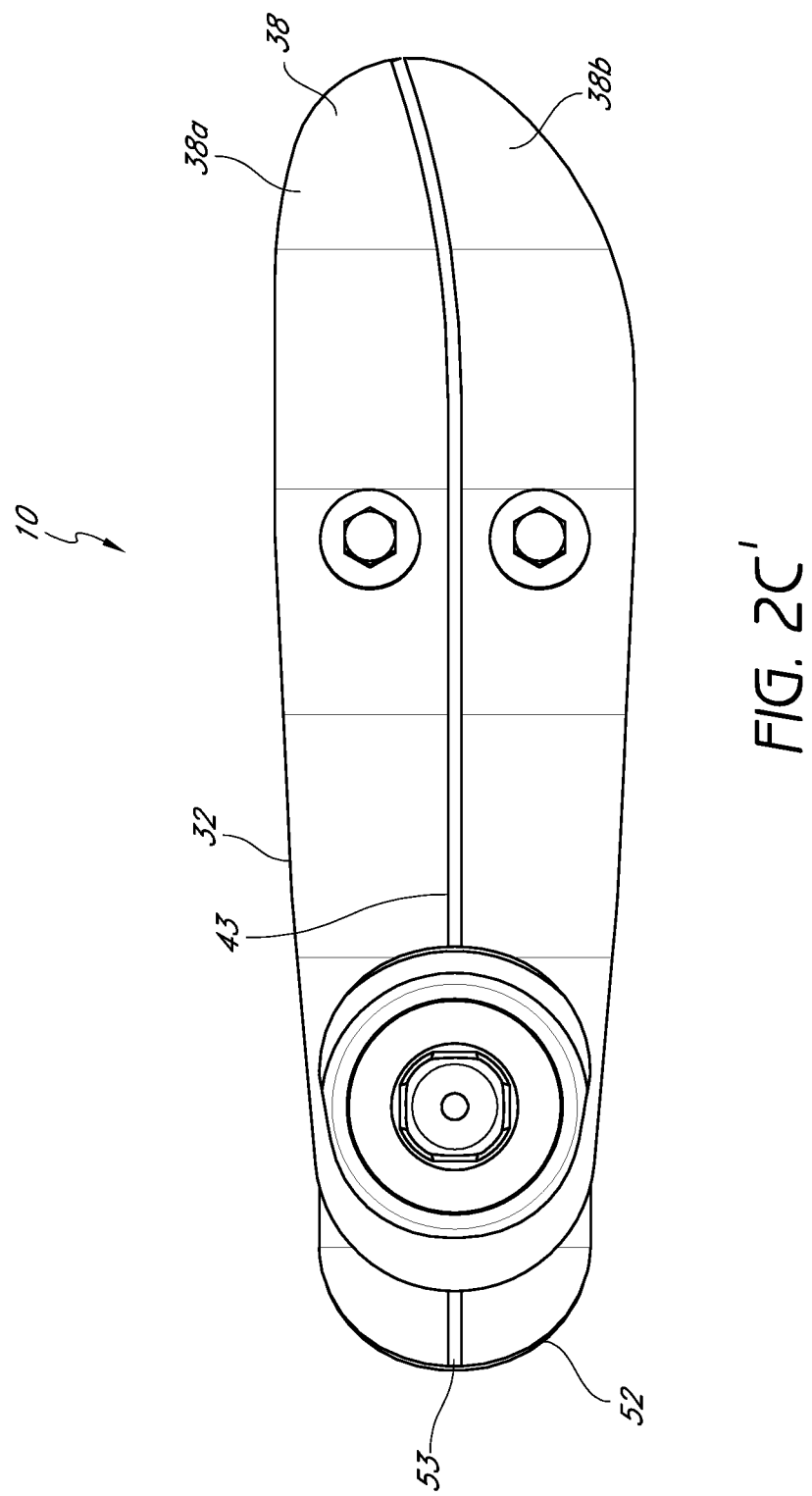

FIGS. 2A-2L" illustrate different views and features of a second foot prosthesis having one or more splits (preferably curved) according to embodiments of the present application. FIGS. 2A and 2B illustrate another embodiment of a prosthetic foot 10 with a curved split. The prosthetic foot 10 includes similar features as the prosthetic foot in FIG. 1A, but does not include a prominent, vertical upper section 46 such that the foot is of a much lower-profile. The lower-profile of the foot allows the foot to be used by amputees with long residual limbs. The upper element 32 illustrated in FIGS. 2A and 2B extends downward and forward from its posterior end first in a generally straight direction to form an inclined upper surface where holes 66 are provided. These holes are configured to attach the inclined portion of the upper element to an attachment adapter such as a male pyramid adapter (not shown). From the inclined upper section, the upper element curves toward the anterior end and toe section 38. In this embodiment, the upper element 32 of the prosthetic foot includes a split 43 that extends from the hole 76 to an anterior edge of the upper element. While portions of the split 43 are substantially straight, the split 43 begins to curve in a medial direction around the toe section 38 (shown best in FIG. 2B). The lower element 52 is configured and connected to the upper element in a similar manner as described with respect to FIGS. 1A and 1B.

FIGS. 2C-2L" illustrate additional embodiments of a prosthetic foot 10 having a much lower profile than the prosthetic foot in FIGS. 1A and 1B. In each of these figures, the prosthetic foot 10 includes an upper element 32 having a toe section 38 attached to a lower element 52; a split 43 in the upper element 32 and a split 53 in the lower element 52; fasteners 31 in attachment holes 36 that connect the upper element 32 to the lower element 52; and an adapter member 77 including a pyramid 81 having a generally flat top surface 81a and at least one side surface 81b. While each of the embodiments of the prosthetic foot 10 in FIGS. 2C-2L" share the above features, additional features are discussed below.

FIGS. 2C-2C''' illustrate a prosthetic foot 10 having a curved split 43 formed in the upper element 32 that curves in a medial direction near the toe region 38. The split 43 begins near a posterior edge of the upper element 32 (which is illustrated as having one or more edges in FIGS. 2C and 2C', and smooth and edgeless in FIGS. 2C" and 2C''') proximate to the adapter member 77. The split 43 begins approximately on a longitudinal axis of the upper element 32 (preferably centered) and travels downwardly down the curved slope of the upper element 32 towards the toe region 38 near the anterior edge of the foot. Near the toe region 38, the split 43 curves inward or medially, to form a big toe region 38a. The toe region 38 at the anterior end of the upper element 32 is asymmetrical, such that the medial blade has the big toe region 38a and the lateral blade has a toe region 38b with a lateral edge that curves inwardly to follow the curvature of the split 43. This results in the toe region 38a having an anterior edge with a smaller radius of curvature than the anterior edge of the toe region 38b. This also results in the big toe region 38a having an area approximately equal to or larger than the lateral toe region 38b along the curved portion of the split 43.

Figure 2D:
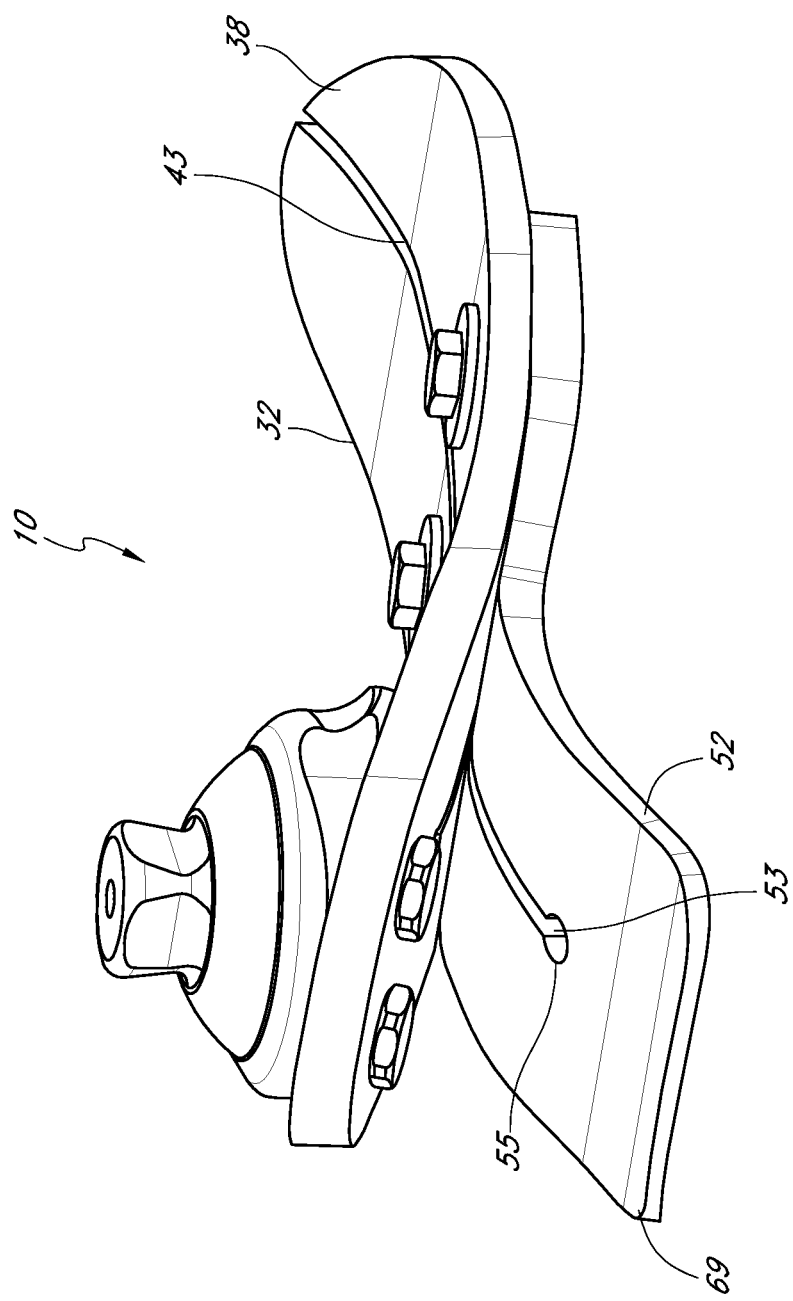

FIGS. 2D-2D" illustrate a prosthetic foot 10 having a split 43 that may or may not be curved formed in the upper element 32 and a split 53 that may or may not be curved formed in the lower element 52. The split 43 formed in the upper element 32 may be similar to the curved split described in FIGS. 2C-2C'''. From a posterior to anterior direction, the split 53 in the lower element 52 begins at a lower hole or aperture 55 formed in the lower element 52 near a heel region 69 of the foot but spaced from a posterior end of the lower element 52. While in some embodiments, the lower aperture 55 can be positioned proximately or along a central longitudinal axis of the lower element 52, in other embodiments, the lower aperture 55 can be off-center away from the central longitudinal axis. In such a case, the split 53 can begin near the heel region 69 at a position away from the central longitudinal axis of the lower element 52 and can curve in a medial or lateral direction towards the central longitudinal axis. After curving in a medial or lateral direction, the curved split 53 can straighten out. In some embodiments, the curved portion of the split 53 in the lower element 52 comprises between about 1/10 to 1/2 or more of the overall length of the split.

Figure 2E:
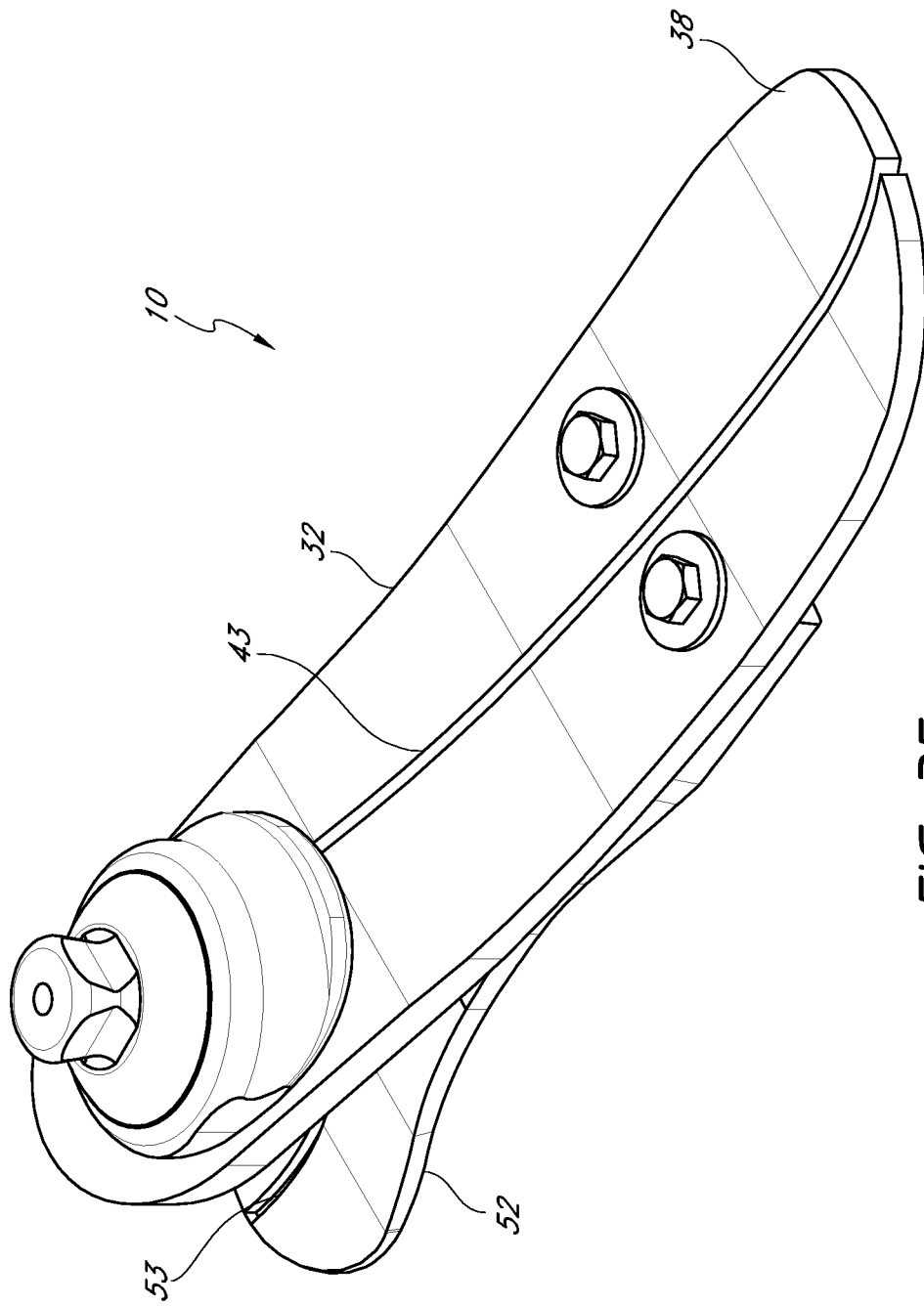

FIGS. 2E-2E''' illustrate a prosthetic foot 10 having a split 43 formed in the upper element 32 that include one or more straight portions that are "askew" (e.g., in a crooked position not parallel with a longitudinal axis of the prosthetic foot or the upper or lower elements). In one embodiment, from a posterior to anterior direction, the prosthetic foot 10 can include a split 43 that begins askew and subsequently straightens in a direction substantially parallel to a central longitudinal axis of the foot. The portion of the split 43 that is askew can extend a majority of the length of the prosthetic foot, as measured from a posterior edge to an anterior edge, as shown in FIG. 2E'. In some embodiments, as shown in FIGS. 2E'-2E''', the prosthetic foot 10 can include a split 43 that is straight and askew throughout a majority of its entire length, as measured from a posterior edge to an anterior edge. The split 43 can be straight and askew throughout an entire length of the foot in some embodiments.

Figure 2F:
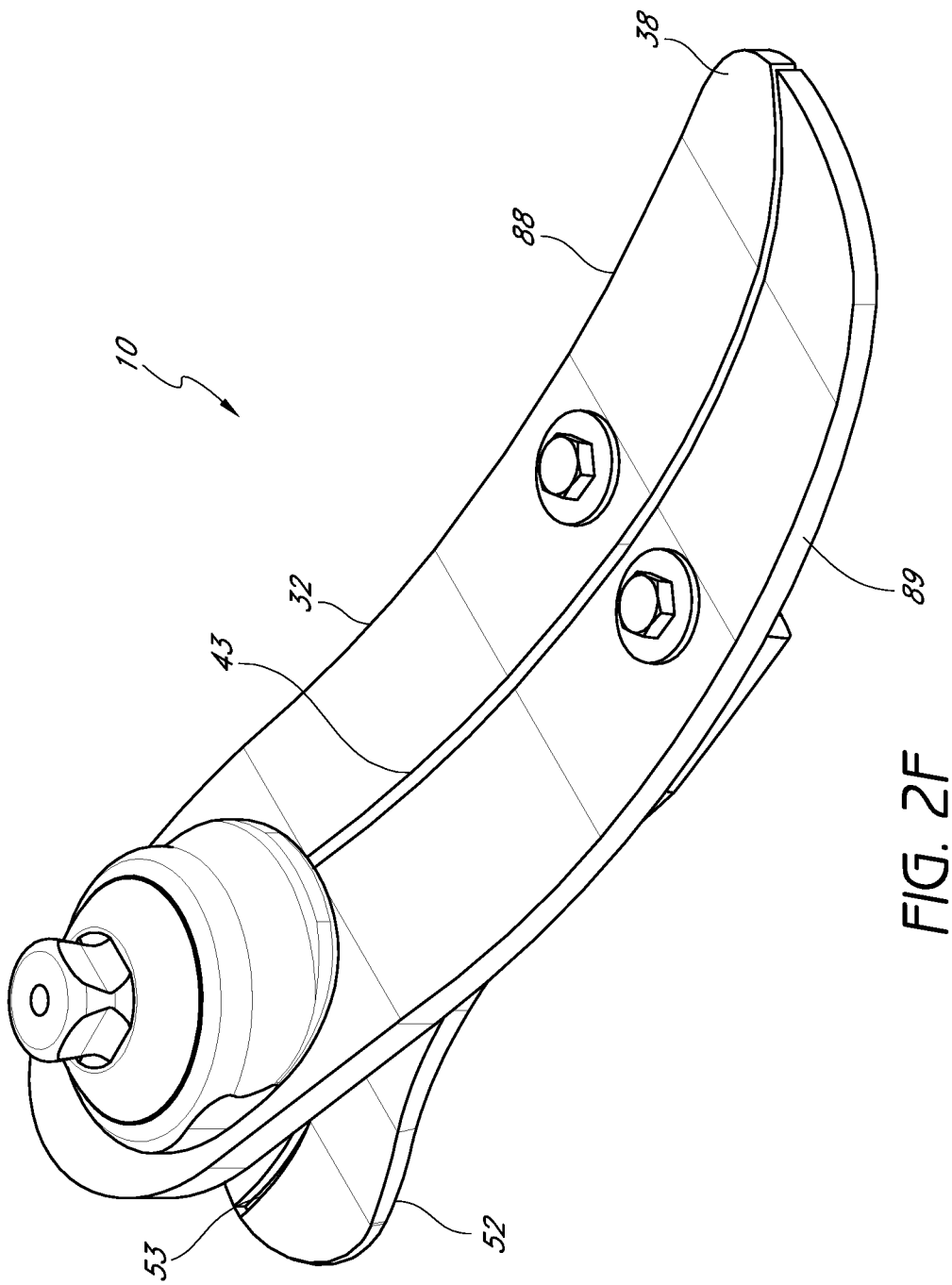
Figure 2F:
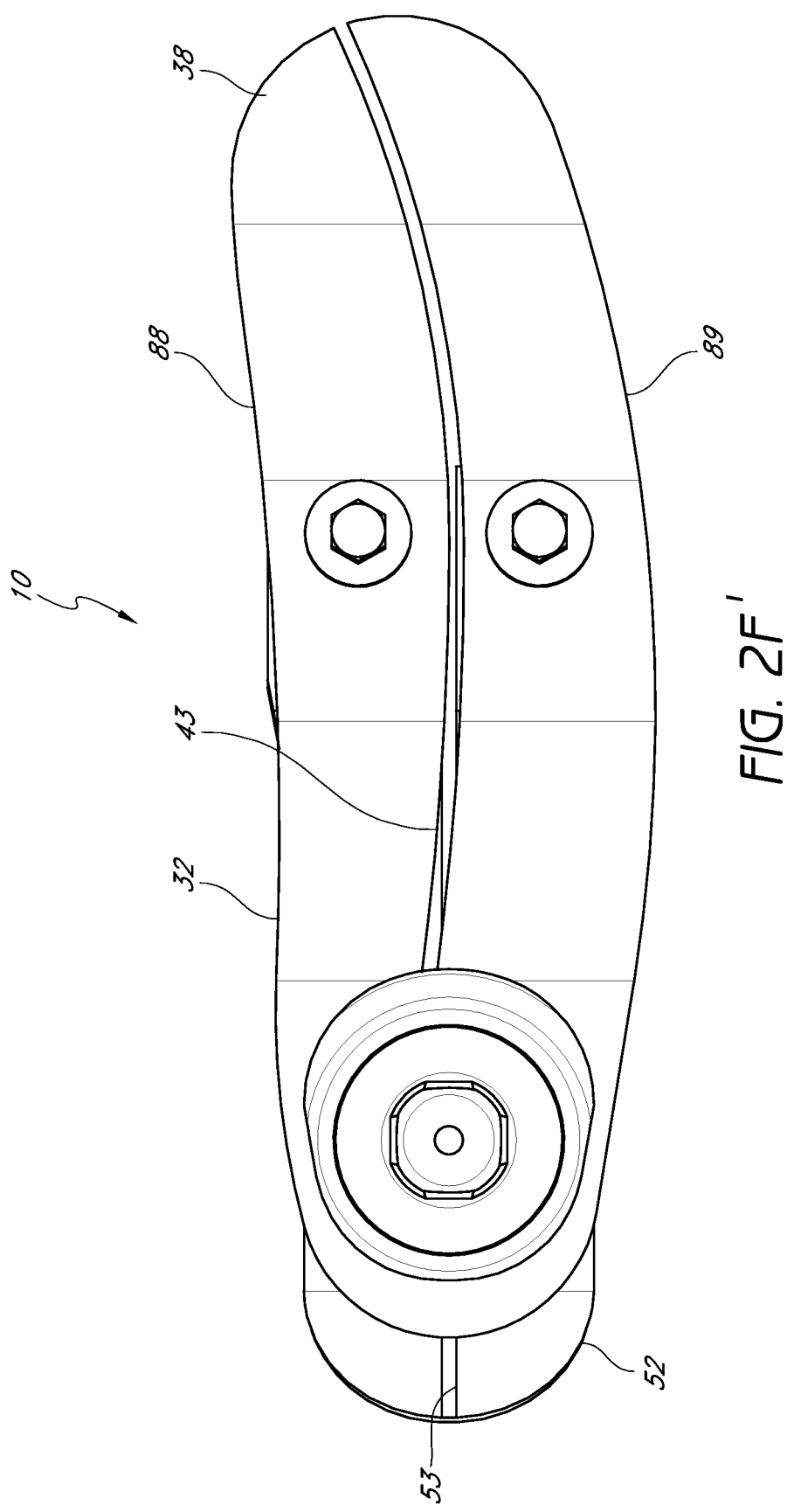

FIGS. 2F-2F''' illustrate a prosthetic foot 10 having an upper element 32 with a curved split 43, and a medial edge 88 and a lateral edge 89 that substantially follow the curvature of the curved split 43, thereby resembling a "banana." While in FIGS. 2F-2F''', both the medial edge 88 and the lateral edge 89 substantially follow the curvature of the curved split 43, in some embodiments, only one of either the medial edge 88 or lateral edge 89 substantially follows the curvature of the curved split 43. In addition, in other embodiments, the prosthetic foot 10 can include an upper element 32 having a curved split 43 and medial and/or lateral edges that are curved, but do not follow the curvature of the curved split 43. The curved split may 43 may be continuously curved substantially over its entire length, beginning at a location spaced anteriorly from the posterior end of the upper element to an anterior edge of the upper element.

Figure 2G:
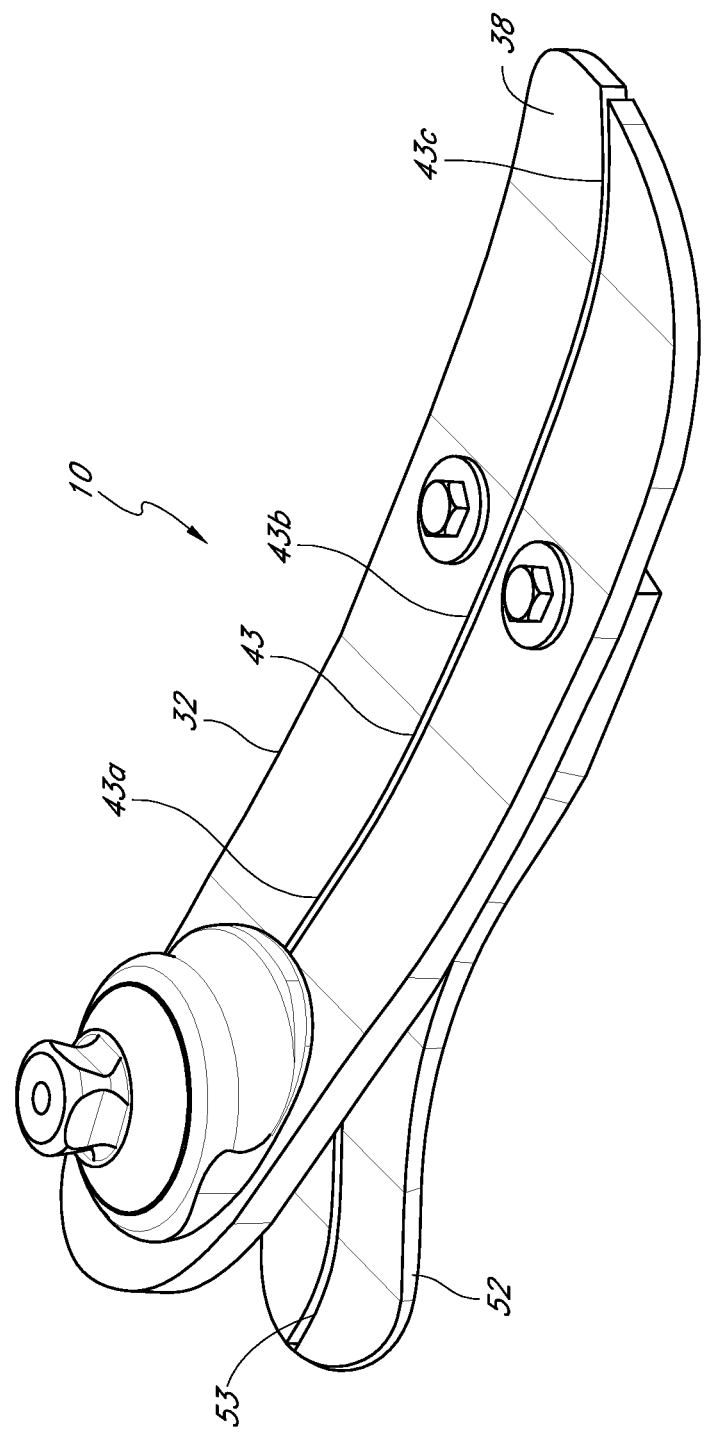
Figure 2G:
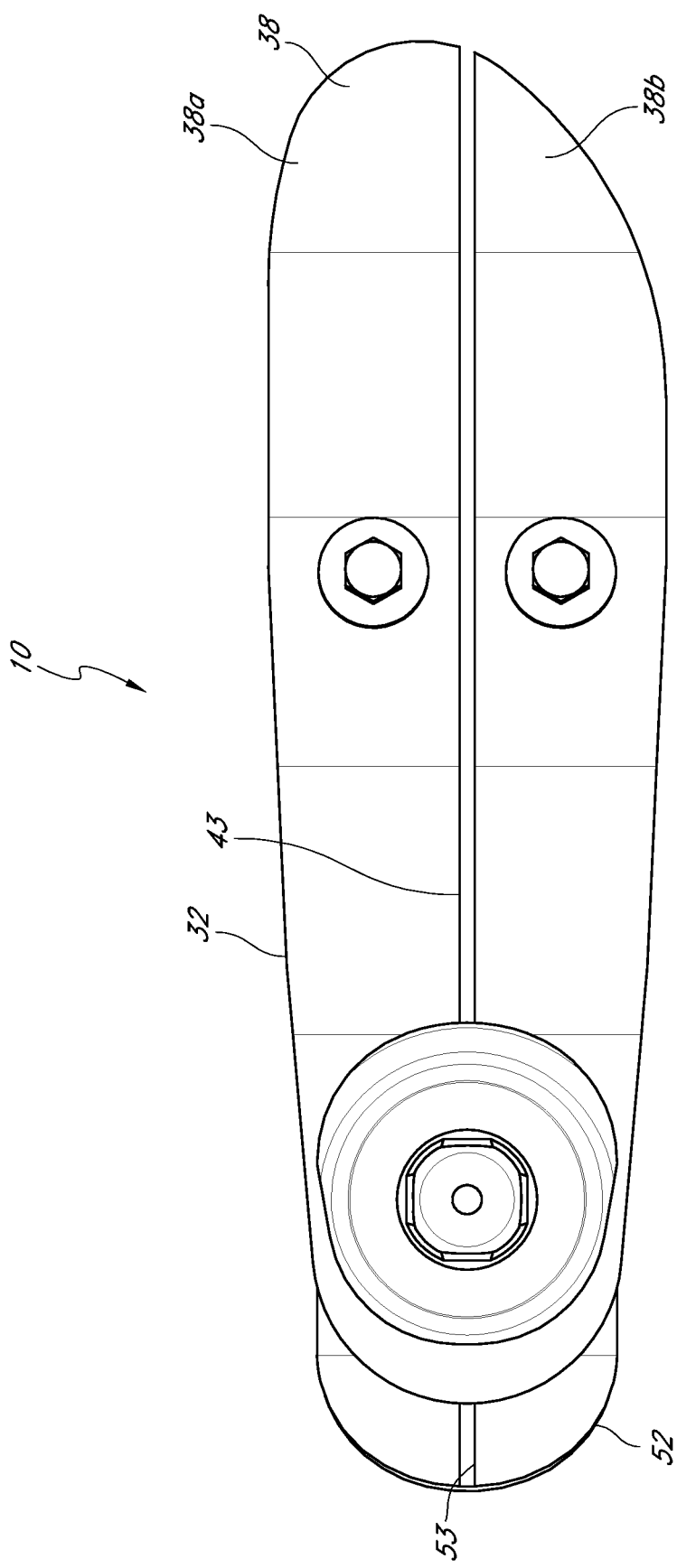
Figure 2G:
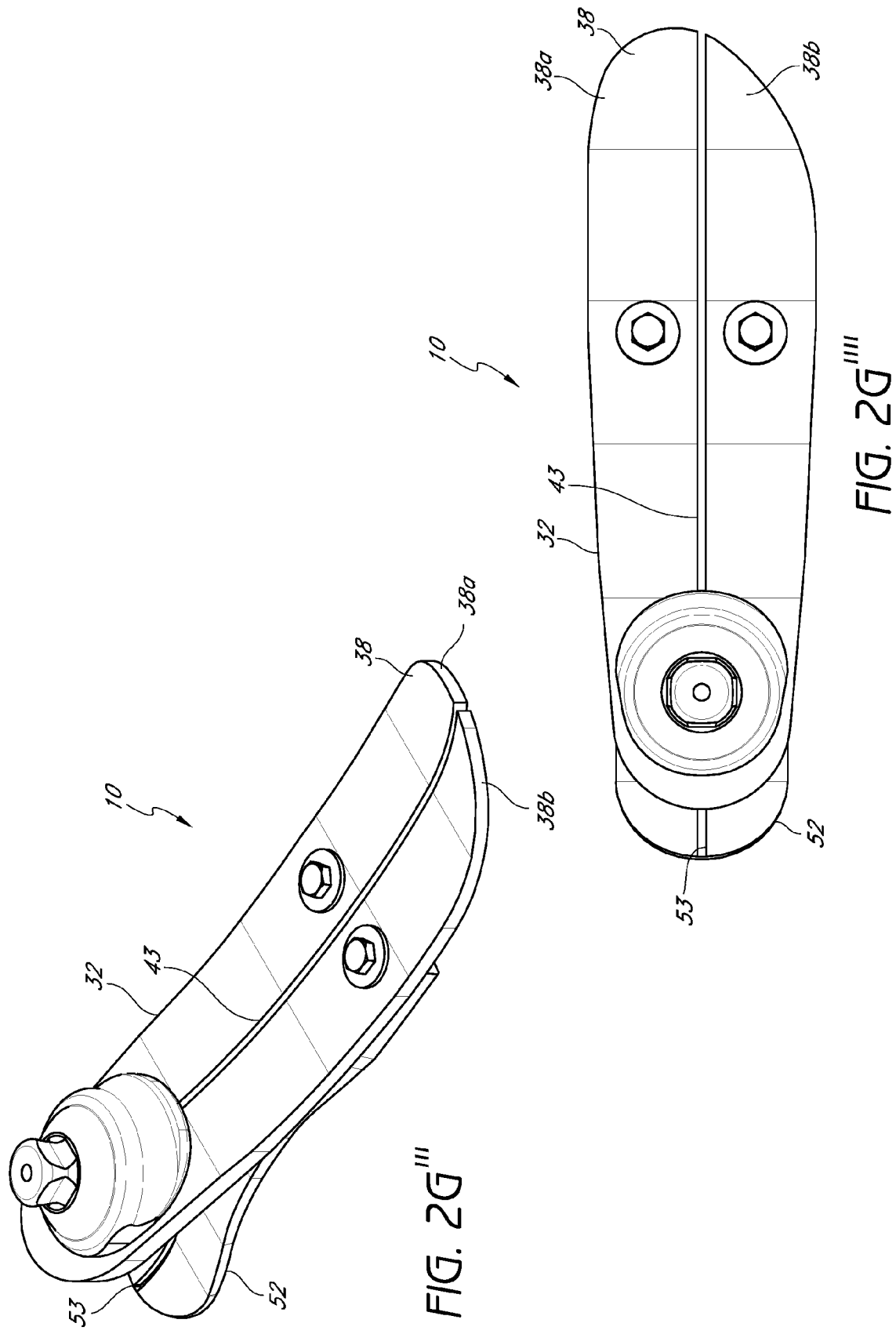

FIGS. 2G-2G'''' illustrate a prosthetic foot 10 comprising an upper element 32 including a split 43. In one embodiment illustrated in FIG. 2G'', the split 43 as illustrated in FIG. 2G may be completely straight along the length of the upper element. Alternatively, as shown in FIGS. 2G and 2G', the split 43 may have a section 43a that is askew toward a medial or lateral direction, followed by a section 43b that is substantially straight, followed by a section 43c that is askew toward a medial or lateral direction. Thus, a prosthetic foot 10 can include a single split 43 having multiple curves or directions. For example, in some embodiments, in a posterior to anterior direction, a split 43 can begin askew in a direction towards a lateral or medial edge of the foot, then can curve and straighten in a direction parallel to a central longitudinal axis of the foot, and then can once again curve and travel in an askew direction toward a lateral or medial edge of the foot.

As shown in FIGS. 2G''-2G'''', a prosthetic foot 10 is illustrated including an upper element 32 having a substantially straight split 43 and a lower element 52 having a substantially straight split 53. The split 43 in the upper element 32 is substantially aligned with the split 53 in the lower element 52. In the embodiment illustrated, the toe region 38 of the upper element 32 is asymmetrical so that a medial or lateral blade of the upper element is longer than the other blade, and at the toe region 38 of the upper element, the toe region of one of the blades 38b has a larger radius of curvature than the toe region of the other blade 38a. In some embodiments, the split 43 divides the upper element such that a first blade has a rounded big toe region 38a that extends anterior to the anterior end of the split, forming an obtuse angle at the anterior end of the split. A second blade has a toe region 38b that forms an acute angle at the anterior end of the split. In this embodiment, the toe region 38a has a greater area than the toe region 38b.

Figure 2H:
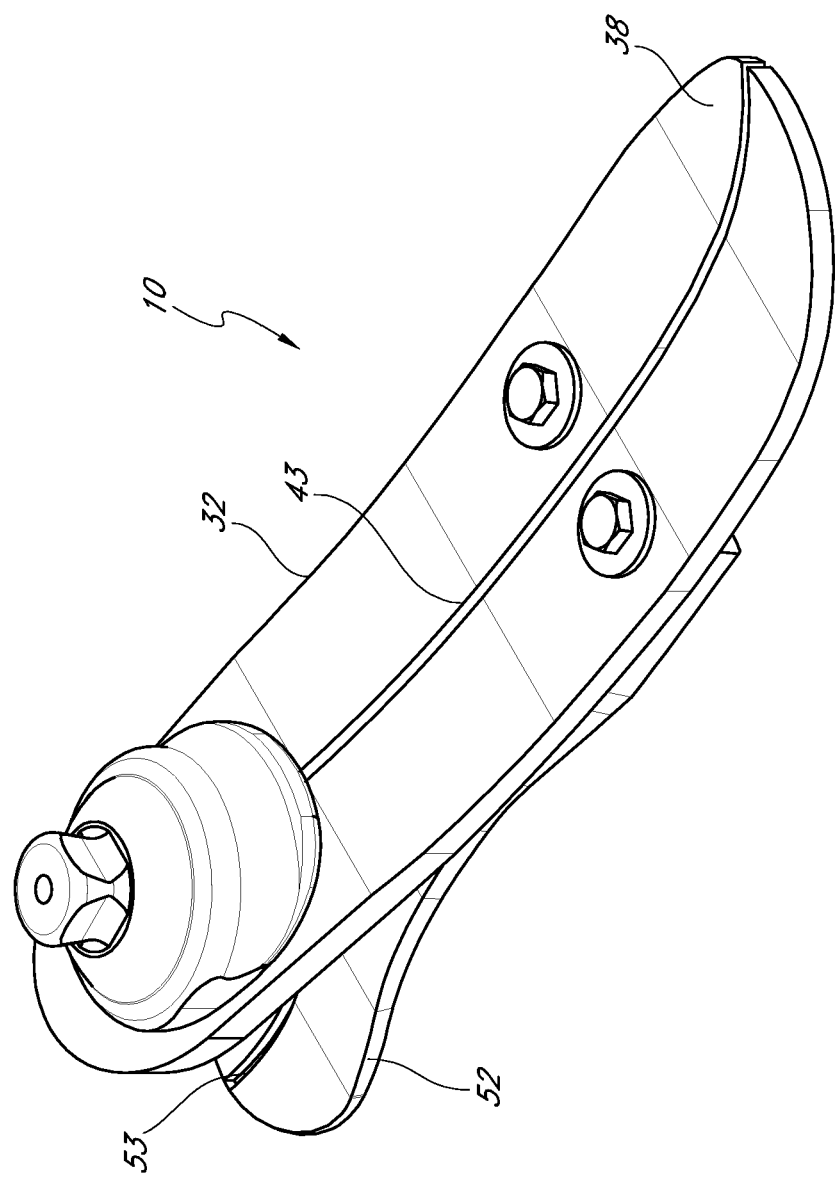
Figure 2H:
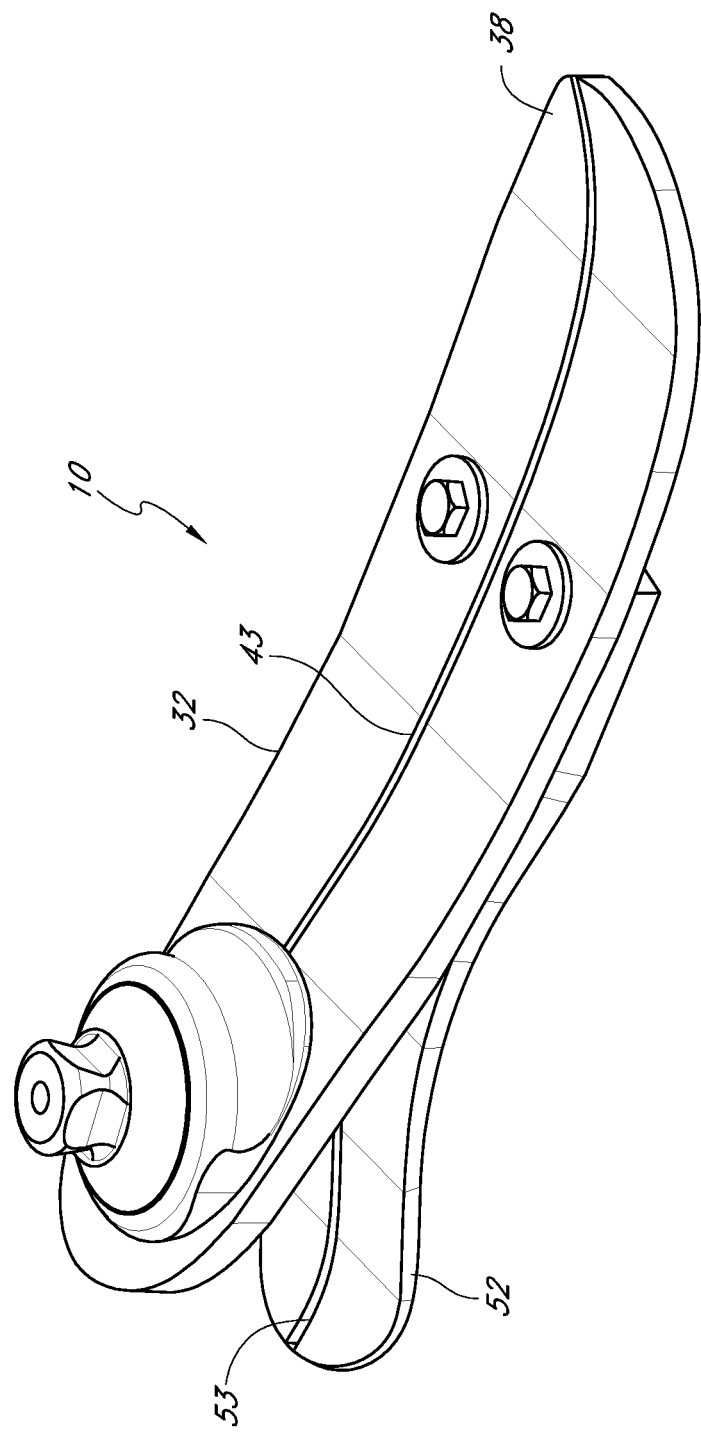
Figure 21:
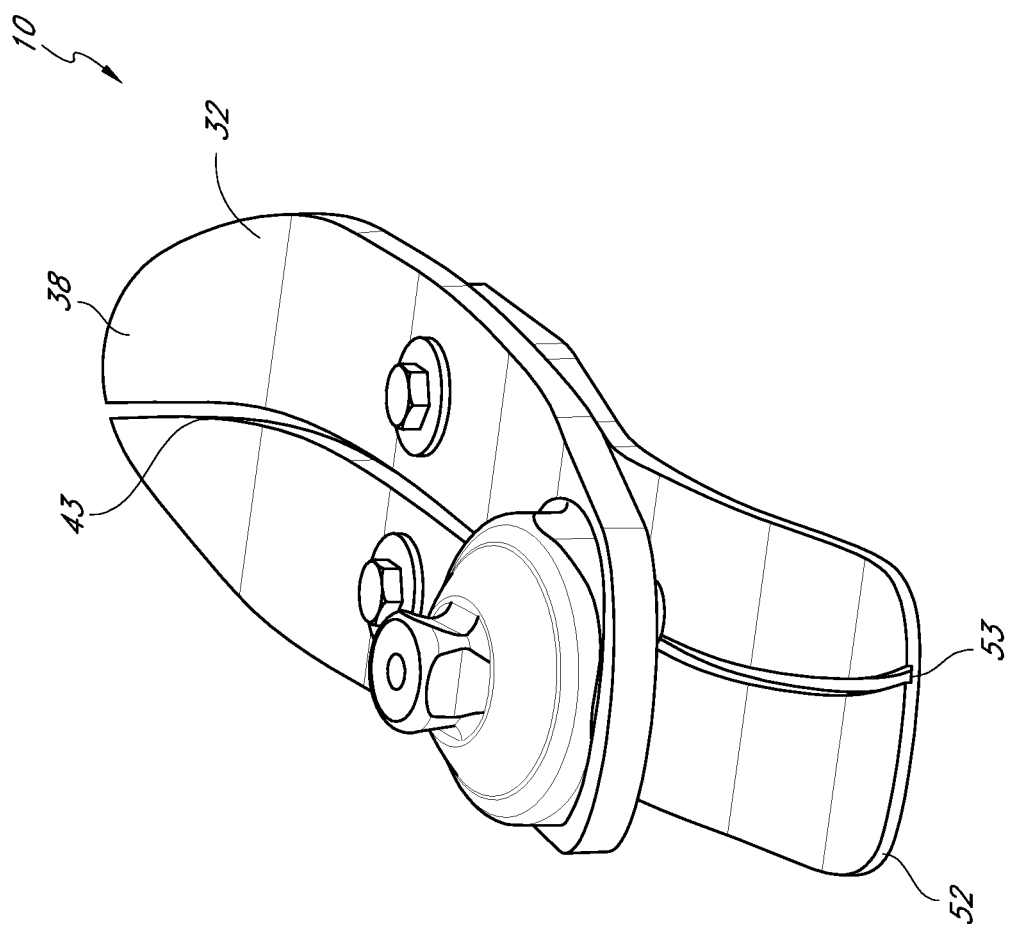
Figure 21:
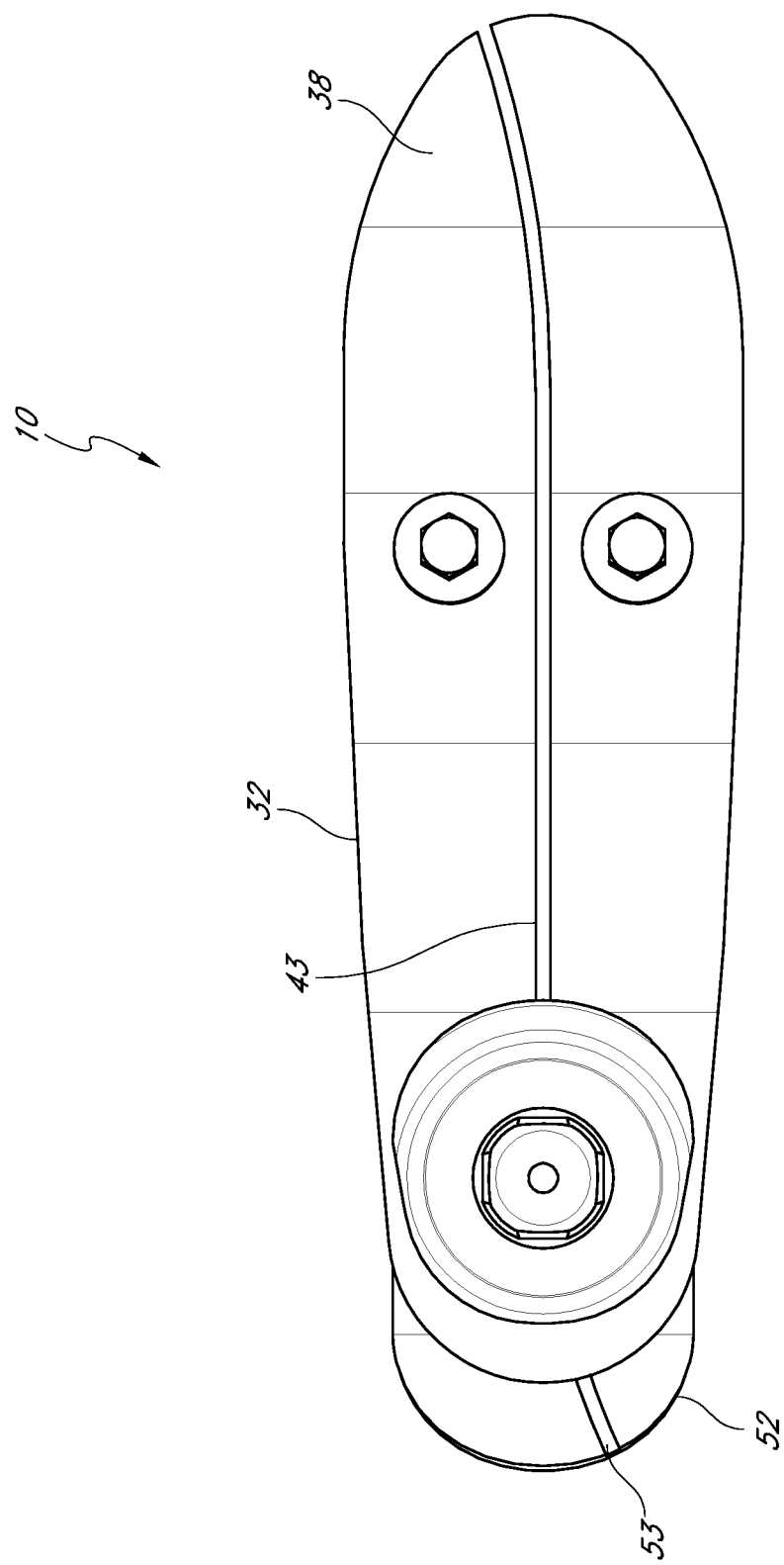

FIGS. 2H-2H''' illustrate a prosthetic foot 10 including an upper element 32 having a curved split 43. From a posterior to anterior direction, the curved split 43 begins substantially straight then curves in a medial direction towards a toe region 38. While the curved split 43 in FIGS. 2H-2H''' is similar to that illustrated in FIGS. 2C-2C''', the toe region 38 is generally symmetrical along its medial and lateral edges, so that the toe region 38a toward which the split 43 curves has a smaller area than the toe region 38b. This results in a much narrower medial blade in the toe section 38a.

FIGS. 2I-2I'''' illustrate a prosthetic foot 10 having a curved split 53 on a lower element 52 that extends an entire length from a posterior edge to an anterior edge of the lower element 52. As shown in FIGS. 2I-2I''', the curved split 53 on the lower element 52 can be paired with a curved split 43 on the upper element 32. In some embodiments, both the curved split 43 on the upper element 32 and the curved split 53 on the lower element extend from a posterior edge to an anterior edge of their respective upper and lower elements. As illustrated, the split 43 on the upper element is spaced from a posterior edge of the upper element. In some embodiments, the curved split 53 on the lower element 52 substantially matches the curvature of the curved split 43 on the upper element 32, while in other embodiments, the curved splits may be asymmetrical. As illustrated, the split 53 on the lower element may curve in an anterior-to-posterior direction toward one side of the prosthetic foot, e.g., the lateral side, while the split 43 on the upper element may curve in a posterior-to-anterior direction toward the other side of the prosthetic foot, e.g., the medial side. As illustrated, the anterior end of the split 53 may be located along a central longitudinal axis of the prosthetic foot and may be aligned underneath a straight portion of the split 43 of the upper element. In some embodiments, the curved split 53 on the lower element 52 can be paired with a split 43 on the upper element 32 that is substantially straight over the entire length of the upper element.

Figure 2J:
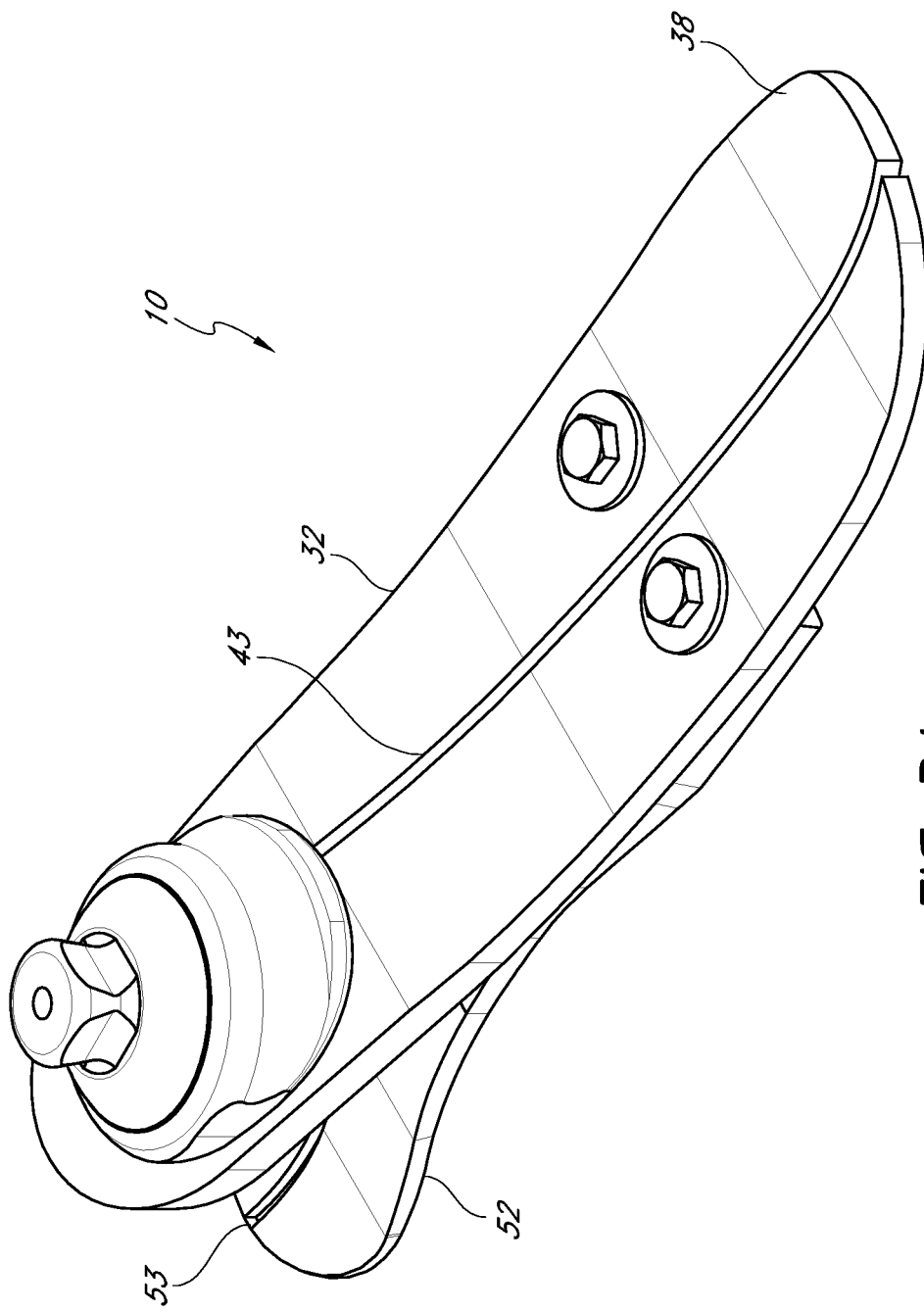
Figure 2J:
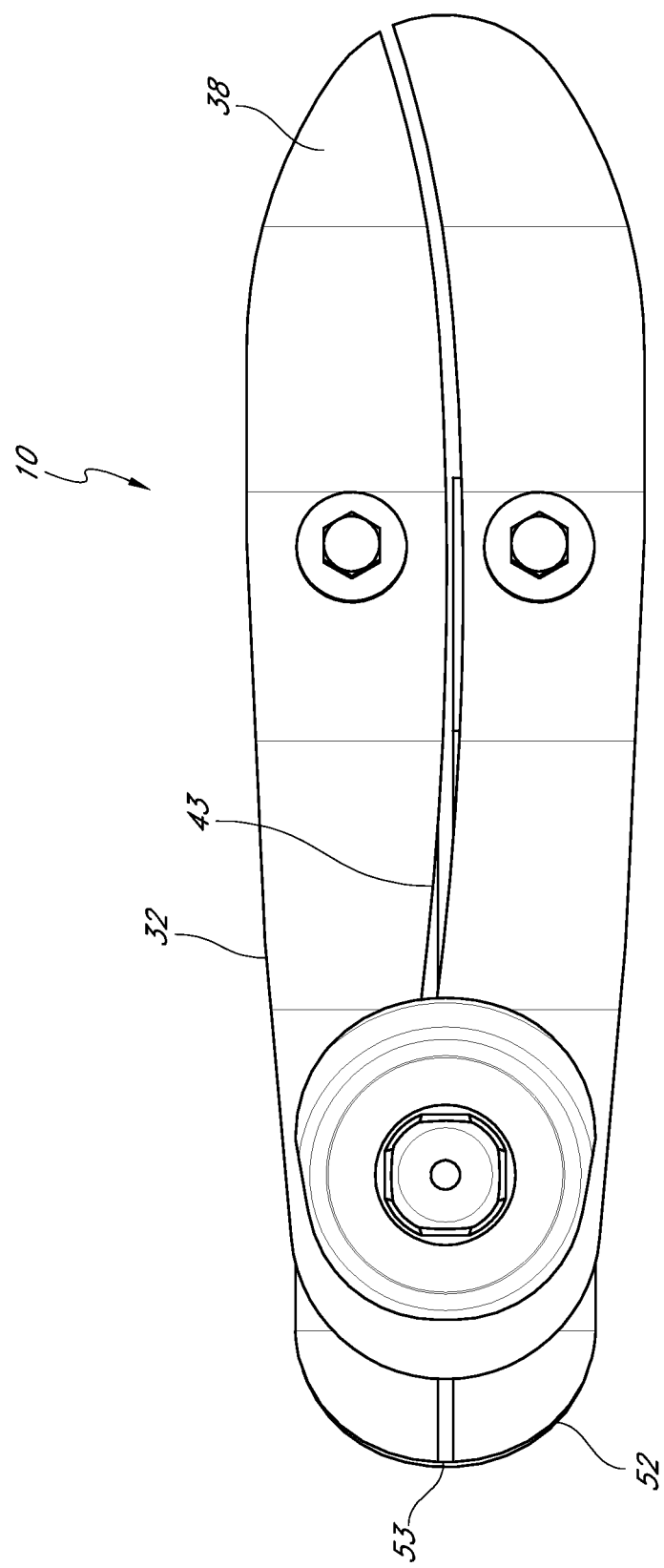

FIGS. 2J-2J''' illustrate a prosthetic foot 10 having a split 43 with a continuous curvature over substantially its entire length on the upper element 32, but with the upper element being substantially symmetrical on its medial and lateral edges. From a posterior to anterior direction, the curved split 43 can begin in a position off-center from a central longitudinal axis of the upper element 32, can curve inward toward the central longitudinal axis, and can curve again outwardly to a position off-center from the central longitudinal axis. In contrast to some of the other embodiments, such as shown in FIGS. 2E and 2G, in which the split 43 changes abruptly from one direction to another thereby forming a noticeable edge, the split 43 in FIGS. 2J-2J''' has smooth curves that are edgeless.

Figure 3C:
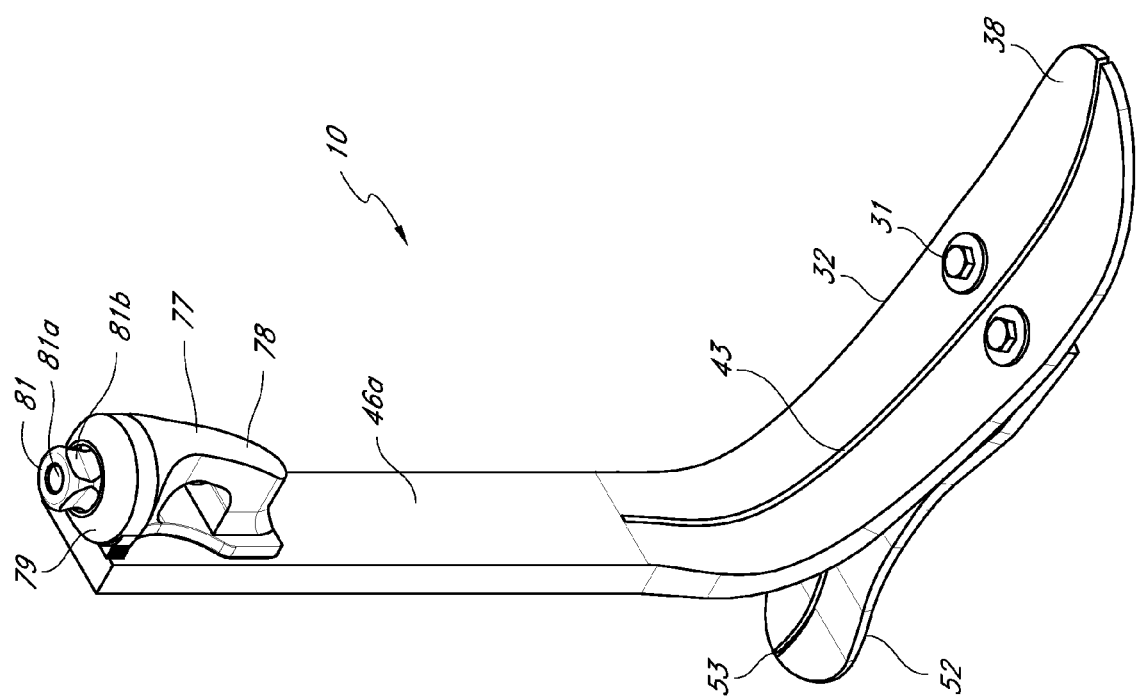
Figure 3D:
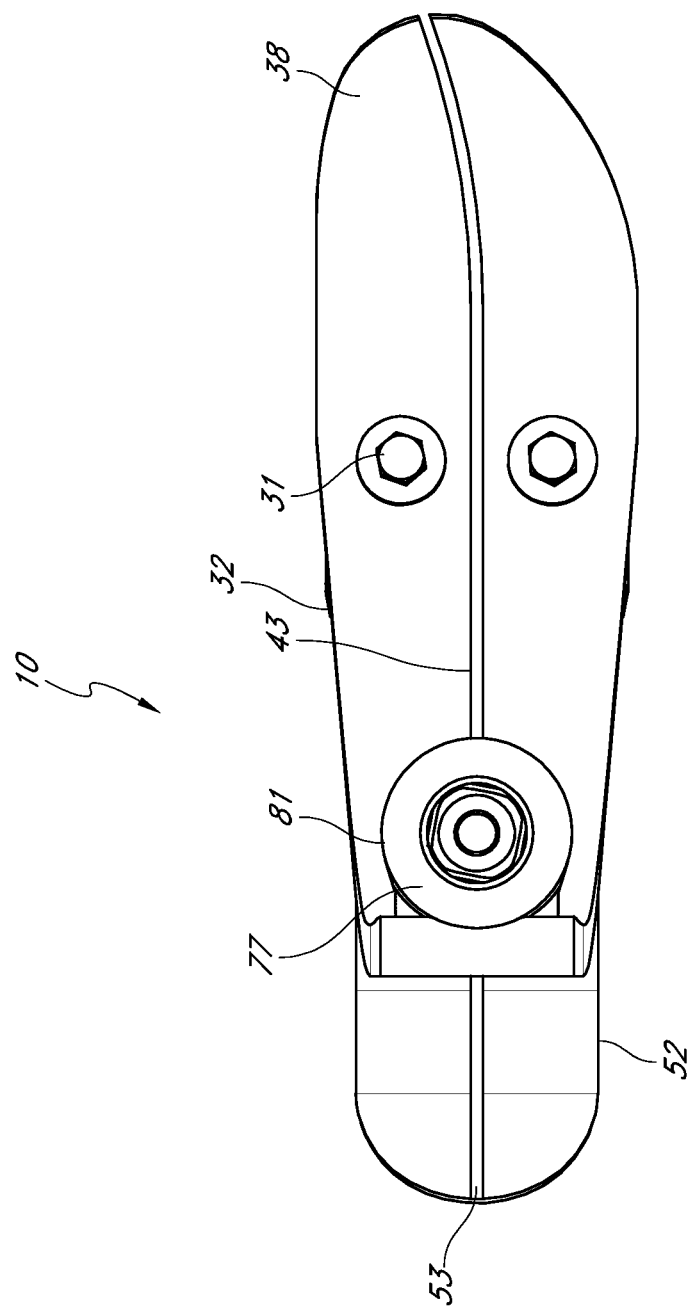

FIGS. 3A-3F illustrate different views and features of a third foot prosthesis having one or more splits (preferably curved) according to embodiments of the present application. FIGS. 3A and 3B illustrate yet another embodiment of a prosthetic foot 10 with a curved split. As shown in FIG. 3A, the prosthetic foot 10 includes an upper vertical portion 46a that is of a length much greater than the embodiment in FIG. 1A. In some embodiments, the upper vertical portion 46a can have a length of between about 5 and 17 inches. One advantage of having an upper vertical portion 46a of relatively long length is that it can be used as a standard component for a variety of amputees of different heights by trimming and fitting as required. In some embodiments, the upper vertical portion 46a comprises a solid, monolithic member, while in other embodiments, the upper vertical portion 46a can comprise a series of linking members such that the length of the member can be easily adjusted.

While the upper portion 46a includes hole 76, no other holes (e.g., upper attachment holes) are visible on the upper portion 46a; however, in other embodiments, one or more upper attachment holes are provided. The hole 76 is located between about ⅔ to ⅞ of the distance down from the top of the upper portion 46. The split 43 extends from the hole and downward toward the toe section 38. In this embodiment, portions of the split 43 are substantially straight but begin to curve proximate to the toe section 38 in a medial direction.

FIGS. 3C-3F illustrate additional embodiments of the third foot prosthesis according to embodiments of the present application. The prosthetic foot 10 includes an upper element 32 and a lower element 52. The upper element 32 includes a curved split 43 that separates the upper element into an upper medial blade and an upper lateral blade, while the lower element 52 includes a split 53 that separates the lower element 52 into a lower medial blade and a lower lateral blade. An adapter member 77 is operably connected to an upper section 46a of the upper element 32 via one or more upper attachment holes (not shown). Fasteners 31 are inserted through lower attachment holes 36 to attach the upper member 32 to the lower member 52.

As shown in FIGS. 3C-3F, the adapter member 77 includes a lower portion 78 and an upper portion 79. The lower portion 78 of the adapter member 77 is operably connected to the upper section 46a of the upper element 32. The upper portion 79 comprises a pyramid 81 adapted to connect to a pylon or other prosthesis (not shown). As shown in FIG. 3E, the pyramid 81 has a generally flat top surface 81a and at least one side surface 81b. In the illustrated embodiments, the side surface 81b comprises four generally flat faces inclined relative to a longitudinal axis through the flat top surface 81a. However, one skilled in the art will appreciate that other shapes and surfaces can be provided for the adapter member 77, so long as it serves to connect the prosthetic foot 10 to a pylon or other prosthesis. In some embodiments, the adapter member 77 is removably connected to the upper element 32, while in other embodiments, the adapter member 77 is permanently attached to the upper element 32 of the prosthetic foot 10.

FIGS. 4A and 4B illustrate another embodiment of a prosthetic foot with a curved split. As shown in FIG. 4A, the prosthetic foot 10 includes similar features as the prosthetic foot in FIG. 1A, including an upper element 32 having a hole 76 from which the curved split 43 extends. The hole 76 is located between about ½ to ¾ of the distance down from the top of the upper portion 46. The split 43 extends from the hole and downward toward the toe section 38. In this embodiment, portions of the split 43 are substantially straight but begin to curve proximate to the toe section 38 in a medial direction.

The upper element 32 also includes a posterior curve 88 that is formed between an upper portion 46b of the prosthetic foot and the toe section 38. As shown in FIG. 4A, the upper element 32 of the prosthetic foot is formed of a vertical upper portion 46b that smoothly transitions downwardly and posteriorly into the curve 88 before then curving anteriorly and downwardly towards the toe region 38. While in some embodiments, the posterior curve 88 is of a material similar to surrounding sections of the upper element 32, in other embodiments, it is of a different material that is of slightly greater elasticity than surrounding material. The advantage of the posterior curve 88 having a greater elasticity than surrounding portions of the upper element is that it is better able to absorb loads that forms or transmitted to this region.

The various splits described above (including those having straight portions, curved portions and askew portions) can be used with a variety of other prosthetic feet in addition to those described above. For example, the curved split can be used with the prosthetic feet described in U.S. patent application Ser. No. 07/029,947, filed on Mar. 26, 1987, now issued as U.S. Pat. No. 4,822,363, U.S. patent application Ser. No. 07/293,824, filed on Jan. 5, 1989, now issued as U.S. Pat. No. 5,037,444, U.S. patent application Ser. No. 07/337,374, filed on Apr. 13, 1989, now issued as U.S. Pat. No. 5,181,932, U.S. patent application Ser. No. 10/642,125, filed on Aug. 15, 2003, and U.S. patent application Ser. No. 10/674,736, filed on Sep. 30, 2009, all of which are incorporated by reference in their entireties.

It will be apparent to those skilled in the art that various modifications and variations can be made in the present invention without departing from the scope or spirit of the invention. Thus, it is intended that the present invention cover the modifications and variations of this invention provided that they come within the scope of the appended claims or their equivalents.

What is claimed is:

1. A prosthetic foot comprising: an upper element having a substantially rectangular transverse cross-section and an upper section at a posterior end of the upper element, wherein the upper element extends downward and forward from the upper section to a toe section at an anterior end of the upper element, wherein the upper element includes an upper split that separates the upper element into an upper medial blade and an upper lateral blade, wherein the upper split extends from a location spaced from the posterior end of the upper element to the anterior end of the upper element, wherein the upper split includes a straight portion and a portion that curves in a medial direction, and wherein the upper element includes a medial edge on a medial side of the upper medial blade and a lateral edge on a lateral side of the upper lateral blade that are substantially asymmetrical in the toe section, with the lateral edge having a curvature in the toe section that follows a curvature of the curved portion of the split in the toe section so that the two curvatures correspond; and a lower element having a substantially rectangular transverse cross-section and connected to the upper element, the lower element including a heel section at a posterior end of the lower element and a front section at an anterior end of the lower element.

2. The prosthetic foot of claim 1, wherein the upper split is curved over a length less than its entire length.

3. The prosthetic foot of claim 1, wherein the lower element includes a lower split that separates the lower element into a lower medial blade and a lower lateral blade, wherein the lower split extends from a posterior end of the lower element toward the anterior end of the lower element.

4. A prosthetic foot comprising: an upper element having a substantially rectangular transverse cross-section and an upper section at a posterior end of the upper element, wherein the upper element extends downward and forward from the upper section to a toe section at an anterior end of the upper element, wherein the upper element includes an upper split that separates the upper element into an upper medial blade and an upper lateral blade, wherein the upper split extends from a location spaced from the posterior end of the upper element to the anterior end of the upper element, wherein the upper split comprises a straight portion and a portion that curves in a medial direction, and wherein the upper element includes a medial edge on a medial side of the upper medial blade and a lateral edge on a lateral side of the upper lateral blade that are substantially asymmetrical in the toe section, with the lateral edge having a curvature in the toe section that substantially follows a curvature of the curved portion of the split in the toe section so that the two curvatures correspond; and a lower element having a substantially rectangular transverse cross-section and connected to the upper element, the lower element including a heel section at a posterior end of the lower element and a front section at an anterior end of the lower element, wherein the lower element includes a lower split that separates the lower element into a lower medial blade and a lower lateral blade, wherein the lower split extends from a posterior end of the lower element toward the anterior end of the lower element.

5. A prosthetic foot comprising: an upper element having a substantially rectangular transverse cross-section and an upper section at a posterior end of the upper element, wherein the upper element extends downward and forward from the upper section to a toe section at an anterior end of the upper element, wherein the upper element includes an upper split that separates the upper element into an upper medial blade and an upper lateral blade, wherein the upper split extends from an opening in the upper element spaced from the posterior end of the upper element to the anterior end of the upper element, the upper split including a portion that is substantially straight in a posterior to anterior direction followed by a portion that curves in a medial direction, and wherein the upper element includes a medial edge on a medial side of the upper medial blade and a lateral edge on a lateral side of the upper lateral blade that are substantially asymmetrical in the toe section, with the lateral edge having a curvature in the toe section that generally follows a curvature of the curved portion of the split in the toe section so that the two curvatures correspond; and a lower element having a substantially rectangular transverse cross-section and connected to the upper element, the lower element including a heel section at a posterior end of the lower element and a front section at an anterior end of the lower element, wherein the lower element includes a lower split that separates the lower element into a lower medial blade and a lower lateral blade, wherein the lower split extends from a posterior end of the lower element toward the anterior end of the lower element.

6. The prosthetic foot of claim 5, wherein the upper section includes a substantially vertical portion, and wherein the opening is located on the substantially vertical portion.

7. The prosthetic foot of claim 5, wherein the length of the curved portion of the split is between 10 and about 90 mm.

8. The prosthetic foot of claim 5, wherein the upper element is connected to a pyramid adapter.

9. The prosthetic foot of claim 5, wherein the upper element includes a substantially straight, inclined portion.

10. The prosthetic foot of claim 5, wherein the upper element and lower elements are capable of substantially unconstrained flexing along each of their lengths.

11. The prosthetic foot of claim 5, wherein the lower element includes an arch portion.

12. The prosthetic foot of claim 5, wherein the upper element is bolted to the lower element through a plurality of holes in the upper element and lower element.

13. The prosthetic foot of claim 5, wherein the anterior end of the lower element terminates posterior to the anterior end of the upper element.

14. The prosthetic foot of claim 5, wherein a length of the curved portion of the upper split is between about $1/10$ to $1/4$ of a total length of the upper split.

* * * * *